(12) United States Patent
Alanine et al.

(10) Patent No.: US 6,440,995 B1
(45) Date of Patent: Aug. 27, 2002

(54) QUINOLIN-4-YL DERIVATIVES

(75) Inventors: Alexander Alanine, Riedisheim; Serge Burner, Durmenach-Ferrette, both of (FR); Bernd Buettelmann, Schopfheim (DE); Marie-Paule Heitz Neidhart, Hagenthal la Bas (FR); Georg Jaeschke, Basel (CH); Emmanuel Pinard, Linsdorf (FR); René Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/658,934

(22) Filed: Sep. 11, 2000

(30) Foreign Application Priority Data

Oct. 1, 1999 (EP) .............................................. 99119539

(51) Int. Cl.[7] ...................... A61K 31/47; C07D 215/16; C07D 215/20; C07D 215/38
(52) U.S. Cl. ........................ 514/312; 514/313; 514/314; 546/153; 546/154; 546/159; 546/160
(58) Field of Search ................................ 514/312, 313, 514/314; 546/153, 154, 159, 160

(56) References Cited

U.S. PATENT DOCUMENTS

| | | |
|---|---|---|
| 4,560,692 A | 12/1985 | Field et al. |
| 5,441,963 A | 8/1995 | McDonald et al. ......... 514/311 |
| 5,614,532 A | 3/1997 | Carling et al. .............. 514/312 |

FOREIGN PATENT DOCUMENTS

DE  440 008  5/1927

OTHER PUBLICATIONS

Asthana et al., Indian Journal of Chemistry, vol. 26B, pp. 330–334 (1987).
Desai et al., Indian Journal of Chemistry, vol., 35B, pp. 871–873 (1996).
Baldwin et al., J. Med. Chem., vol. 22(11), pp. 1284–1290 (1979).
Hauser et al., J. Am. Chem. Soc., vol. 70, p. 2402–2404 (1948).
Hauser et al., J. Am. Chem Soc., vol. 77, p. 2851–2852 (1955).
Jones et al., Quinolines. The Chemistry of Heterocyclic Compounds, Wiley, New York, vol. 32, pp. 181–191 (1997).
Jones et al., Quinolines. The Chemistry of Heterocyclic Compounds, Wiley, New York, vol. 32, pp. 195–207 (1997).
Strekowski L., et al., Bioorg. Med. Chem. Letters, vol. 9, No. 13 (1999) pgs. 1819–1824, XP00418845.

*Primary Examiner*—D. Margaret Seaman
(74) *Attorney, Agent, or Firm*—George W. Johnston; Patricia S. Rocha-Tramaloni; Arthur D. Dawson

(57) ABSTRACT

Phenyl substituted quinolin 4-yl derivatives and pharmaceutical compositions with activity as NMDA-receptor subtype selective blockers. The compounds of the invention modulate neuronal activity and plasticity.

35 Claims, No Drawings

QUINOLIN-4-YL DERIVATIVES

BACKGROUND OF THE INVENTION

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, chronic and acute pain.

SUMMARY OF THE INVENTION

The compounds of formula I:

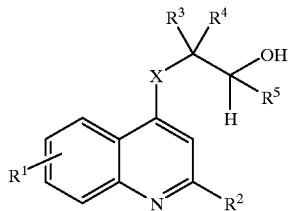

and their salts are distinguished by valuable therapeutic properties. Compounds of the present invention are NMDA (N-methyl-D-aspartate)-receptor subtype selective blockers, which have a key function in modulating neuronal activity and plasticity which makes them key players in mediating processes underlying development of CNS as well as learning and memory formation.

Objects of the invention are the compounds of formula I and pharmaceutically acceptable acid addition salts thereof, the preparation of the compounds of formula I and salts thereof, medicaments containing a compound of formula I or a pharmaceutically acceptable acid addition salt thereof, the manufacture of such medicaments and the use of the compounds of formula I and their pharmaceutically acceptable salts in the control or prevention of illnesses, especially of illnesses and disorders of the kind referred to earlier, and, respectively, for the manufacture of corresponding medicaments.

DETAILED DESCRIPTION OF THE INVENTION

The present invention relates to compounds of formula I:

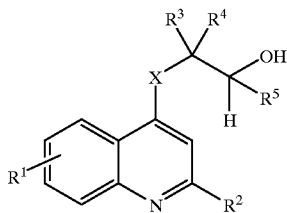

wherein $R^1$ is hydrogen, lower alkyl, lower alkoxy, hydroxy, amino, nitro, cyano, lower alkyl-amino, di-lower alkyl-amino or halogen;

$R^2$ is phenyl, optionally substituted by lower alkyl, lower alkoxy, halogen, trifluoromethyl, amino, lower alkyl-amino or di-lower alkyl-amino, 2,3-dihydro-benzofuran-5-yl, chroman-6-yl, naphthalen-2-yl, indan-5-yl, lower alkenyl-phenyl, 5,6,7,8-tetrahydro-naphthalenyl, 2,3-dihydro-isoindol-2-yl, 1,2,3,4-tetrahydro-naphthalenyl, benzofuran-2-yl, benzo[b]thiophen-2-yl, lower alkyl-phenyl, 3,4-dihydro-1H-isoquinolin-2-yl or thiophen-3-yl;

$R^3$ and $R^4$ are independently from each other hydrogen or lower alkyl;

$R^5$ is hydrogen, lower alkyl, —$CH_2OH$ or —$CH_2NR^6R^7$;

$R^6$ and $R^7$ are independently from each other hydrogen, lower alkyl, —$(CH_2)_n$-phenyl, cycloalkyl, —$(CH_2)_m$-morpholinyl or form together with the N-atom a saturated ring with 4–6 C-atoms;

n is 0–3;

m is 2 or 3;

X is —$NR^8$— or —O—; or

X and $R^5$ are together >$N(CH_2)_2$—; or

X and $R^3$ are together >$N(CH_2)_3$—; and $R^8$ is hydrogen or lower alkyl;

and to pharmaceutically acceptable acid addition salts thereof.

Not encompassed from compounds of formula I are the following specific compounds, which are described in Indian Journal of Chemistry, Vol. 35B, 1996, 871–873 and having an antibacterial activity.

(6-Chloro-2-phenyl-4-quinolinyl)-(+)-2-aminobutanol;
(6-methyl-2-phenyl-4-quinolinyl)-(+)-2-aminobutanol;
(6-methoxy-2-phenyl-4-quinolinyl)-(+)-2-aminobutanol; and
(8-methoxy-2-phenyl-4-quinolinyl)-(+)-2-aminobutanol;

The present invention embraces racemic mixtures and all their corresponding enantiomers.

The following definitions of the terms used in the present description apply irrespective of whether the terms in question appear alone or in combination.

The term "lower alkyl" denotes a straight- or branched-chain alkyl group containing from 1 to 4 carbon atoms, for example, methyl, ethyl, propyl, isopropyl, butyl and the like.

The term "halogen" denotes chlorine, iodine, fluorine and bromine.

The term "lower alkoxy" denotes a group wherein the alkyl residue is as defined above.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Preferred compounds of formula I in the scope of the present invention are those, wherein X is —NH— and $R^5$ is hydrogen, —$CH_2NH_2$, —$CH_3$ or —$CH_2OH$. These are the following compounds:

2-[2-(3,4-dihydro-1H-isoquinolin-2-yl)-quinolin-4-ylamino]-ethanol,
(RS)-1-amino-3-(2-p-tolyl-quinolin-4-ylamino)-propan-2-ol,
(RS)-1-amino-3-[2-(4-methoxy-phenyl)-quinolin-4-ylamino]-propan-2-ol,
S(+)-1-[2-(4-methoxy-phenyl)-quinolin-4-ylamino]-propan-2-ol,
2-[2-(4-methoxy-phenyl)-7-methyl-quinolin-4-ylamino]-ethanol,
(S)-1-[2-(4-methoxy-3-methyl-phenyl)-quinolin-4-ylamino]-propan-2-ol,
2-(7-Methyl-2-p-tolyl-quinolin-4-ylamino)-ethanol,
(S)-1-[2-(3-chloro-4-methyl-phenyl)-quinolin-4-ylamino]-propan-2-ol,
(RS)-3-[2-(3,4-dihydro-1H-isoquinolin-2-yl)-quinolin-4-ylamino]-propane-1,2-diol,
RS)-1-amino-3-[2-(3,4-dihydro-1H-isoqulinolin-2-yl)-quinolin-4-ylamino]-propan-2-ol,
2-[7-methoxy-2-(4-methoxy-phenyl)-quinolin-4-ylamino]-ethanol,
(RS)-1-amino-3-[7-methoxy-2-(4-methoxy-phenyl)-quinolin-4-ylamino]-propan-2-ol or
(RS)-1-amino-3-(7-methoxy-2-p-tolyl-quinolin-4-ylamino)-propan-2-ol.

Compounds of the present invention, in which X is —O— and $R^5$ is —$CH_2NHCH_3$, —$CH_2NH_2$, —$CH_2NHCH(CH_3)_2$ or —$CH_2NH$-cycloalkyl, are further preferred, for example the following compounds:

(RS)-1-(7-methoxy-2-phenyl-quinolin-4-yloxy)-3-methylamino-propan-2-ol,
(RS)-1-amino-3-(2-phenyl-quinolin-4-yloxy)-propan-2-ol,
(RS)-1-isopropylamino-3-(2-phenyl-quinolin-4-yloxy)-propan-2-ol,
(RS)-1-cyclopentylamino-3-(2-phenyl-quinolin-4-yloxy)-propan-2-ol,
(RS)-1-isopropylamino-3-(7-methoxy-2-phenyl-quinolin-4-yloxy)-propan-2-ol,
(RS)-1-methylamino-3-(2-p-tolyl-quinolin-4-yloxy)-propan-2-ol,
(RS)-1-cyclobutylamino-3-(2-phenyl-quinolin-4-yloxy)-propan-2-ol,
(RS)-1-[2-(4-methoxy-phenyl)-quinolin-4-yloxy]-3-methylamino-propan-2-ol,
(RS)-1-methylamino-3-(7-methyl-2-phenyl-quinolin-4-yloxy)-propan-2-ol,
(RS)-1-(7-methoxy-2-p-tolyl-quinolin-4-yloxy)-3-methylamino-propan-2-ol,
(RS)-1-[7-methoxy-2-(4-methoxy-phenyl)-quinolin-4-yloxy]-3-methylamino-propan-2-ol or
(RS)-1-[2-(4-methoxy-phenyl)-7-methyl-quinolin-4-yloxy]-3-methylamino-propan-2-ol.

The afore-mentioned compounds of formula I can be manufactured in accordance with the invention by a) reacting a compound of formula:

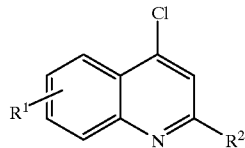

II with an amine of formula:

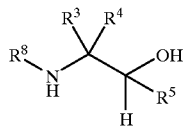

III to a compound of formula:

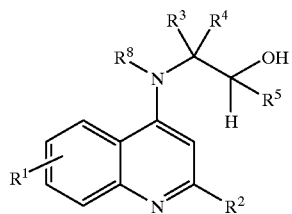

I-1 wherein $R^1$–$R^5$ and $R^8$ have the significances given above, or b) reducing a compound of formula:

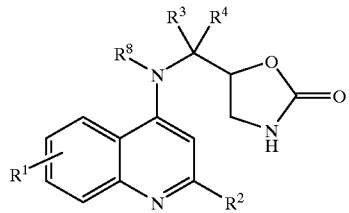

IV with a reducing agent to a compound of formula:

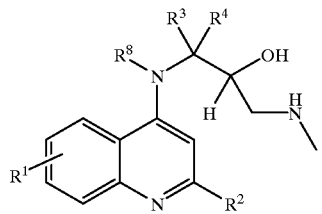

I-12 wherein $R^1$–$R^4$ and $R^8$ have the significances given above, or c) reducing a compound of formula:

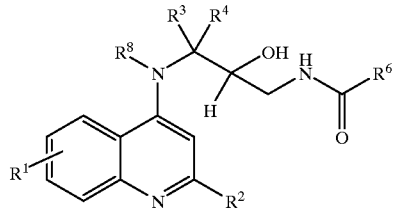

V wherein $R^1$–$R^4$ and $R^8$ have the significances given above and $R^6$ is lower alkyl-phenyl, lower alkyl-morpholino or lower alkyl, to a compound of formula:

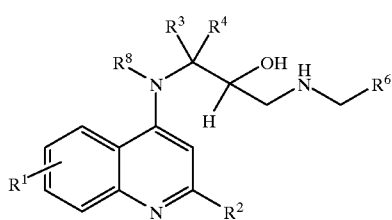

I-13 or (d) reacting a compound of formula:

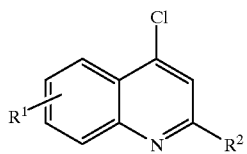

II with a compound of formula:

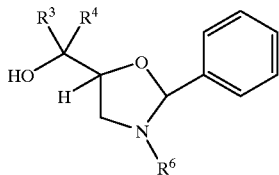

VI to a compound of formula:

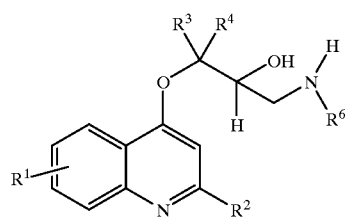

I-2 wherein R¹–R⁴ and R⁶ have the significances given above, or, e) reacting a compound of formula:

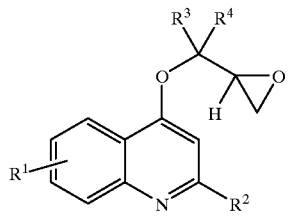

IX with a compound of formula:

H—NR⁶ to a compound of formula:

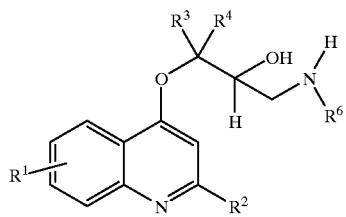

I-2 wherein R¹–R⁴ and R⁶ have the significances given above, or, if desired, modifying one or more substituients within the definitions given above, or if desired, converting the compound of formula I obtained into a pharmaceutically acceptable salt.

In the following the preparation of compounds of formula I are described in more detail:

1. Preparation of Compounds of Formula I, wherein X is —NR⁸—

Scheme 1

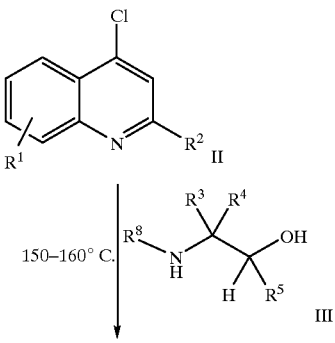

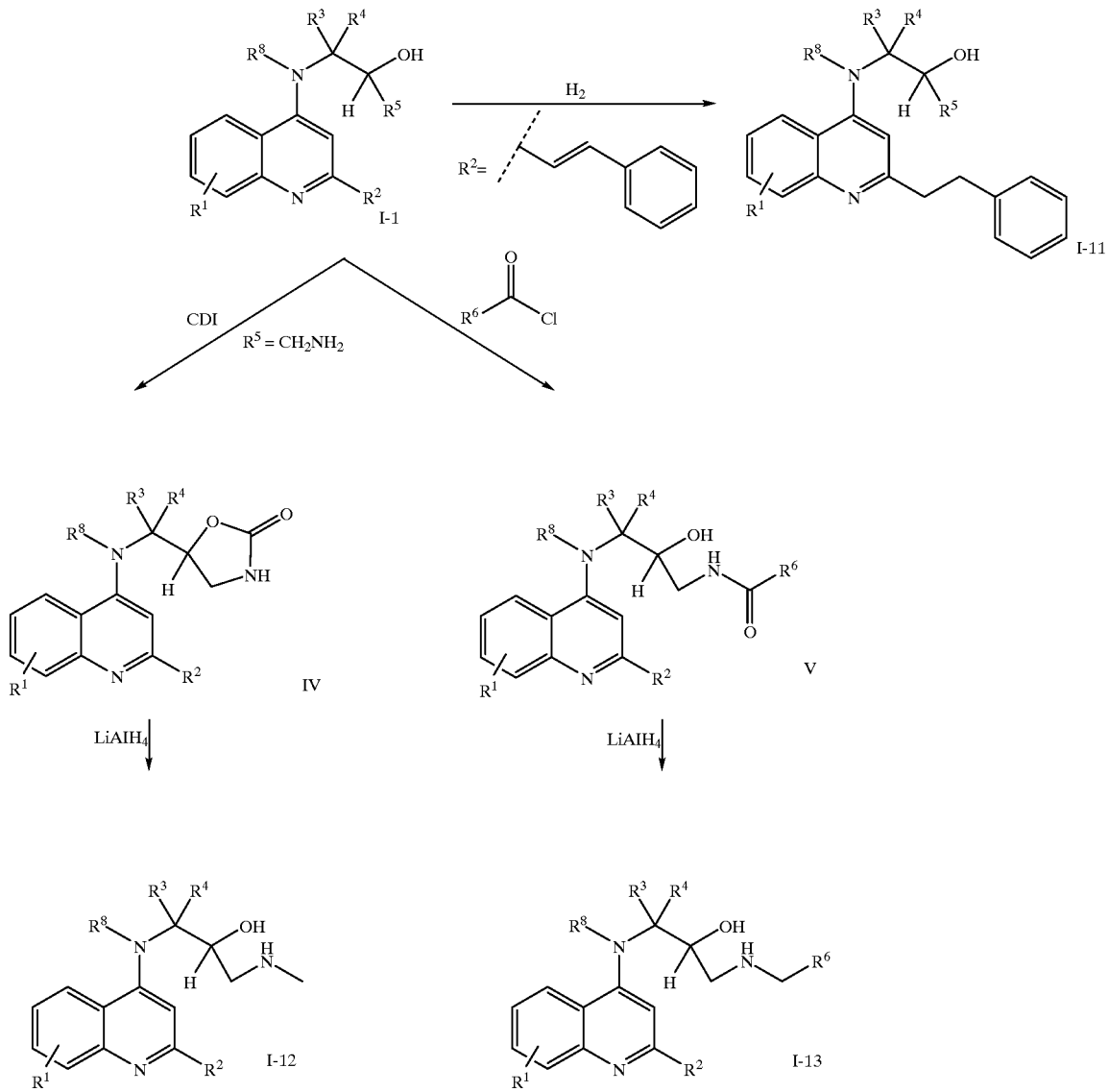

The amino group in 4-position is introduced using known procedures[1], for example by reaction at 150° C. of a corresponding 4-chloro-quinoline with a primary or secondary amine using the neat amine as solvent (scheme 1).

[1]Field, G. F.; Zally, W. J. (Hoffman-La Roche, Inc., USA). U.S. Pat. No. 4,560,692

Introduction of the methyl or higher alkyl groups on the primary group of the side chain was performed using known methods by reduction of an oxazolidin-2-one or an amide (scheme 1). Compounds carring a phenethyl substituents at the 2-position were prepared by hydrogenation of the corresponding styryl derivatives.

2. Preparation of Compounds of Formula I, wherein X is —O—

Scheme 2

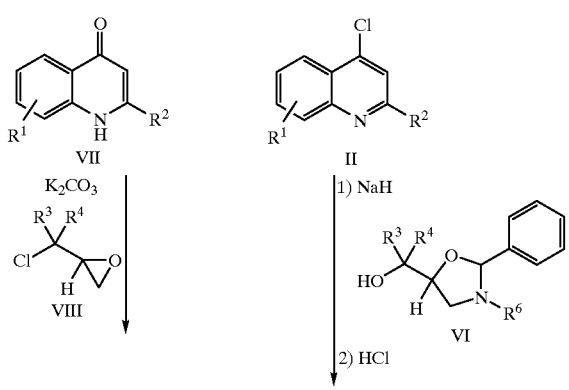

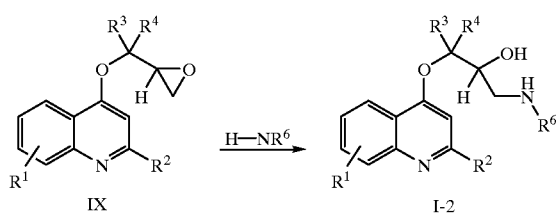

Compounds were made using known procedures either by reacting an amine with an epoxide or by reacting an oxazolidine with a 4-chloro-quinoline in the presence of sodium hydride[2]. Epoxides were prepared using a known procedure by reacting a quinolin-4-one with a chloro epoxide[3] (scheme 2).

[2]Baldwin, J. J.; Lumma, W. C., Jr.; Lundell, G. F.; Ponticello, G. S.; Raab, A. W.; Engelhardt, E. L.; Hirschmann, R.; Sweet, C. S.; Scriabine, A.; J. Med. Chem. (1979), 22(11), 1284–1290.

[3]Asthana, P.; Prasad, M.; R., Shri N.; Indian J.Chem.Sect.B; 26; 1987; 330–334

3. Preparation of the Intermediates of Formula II

Scheme 3

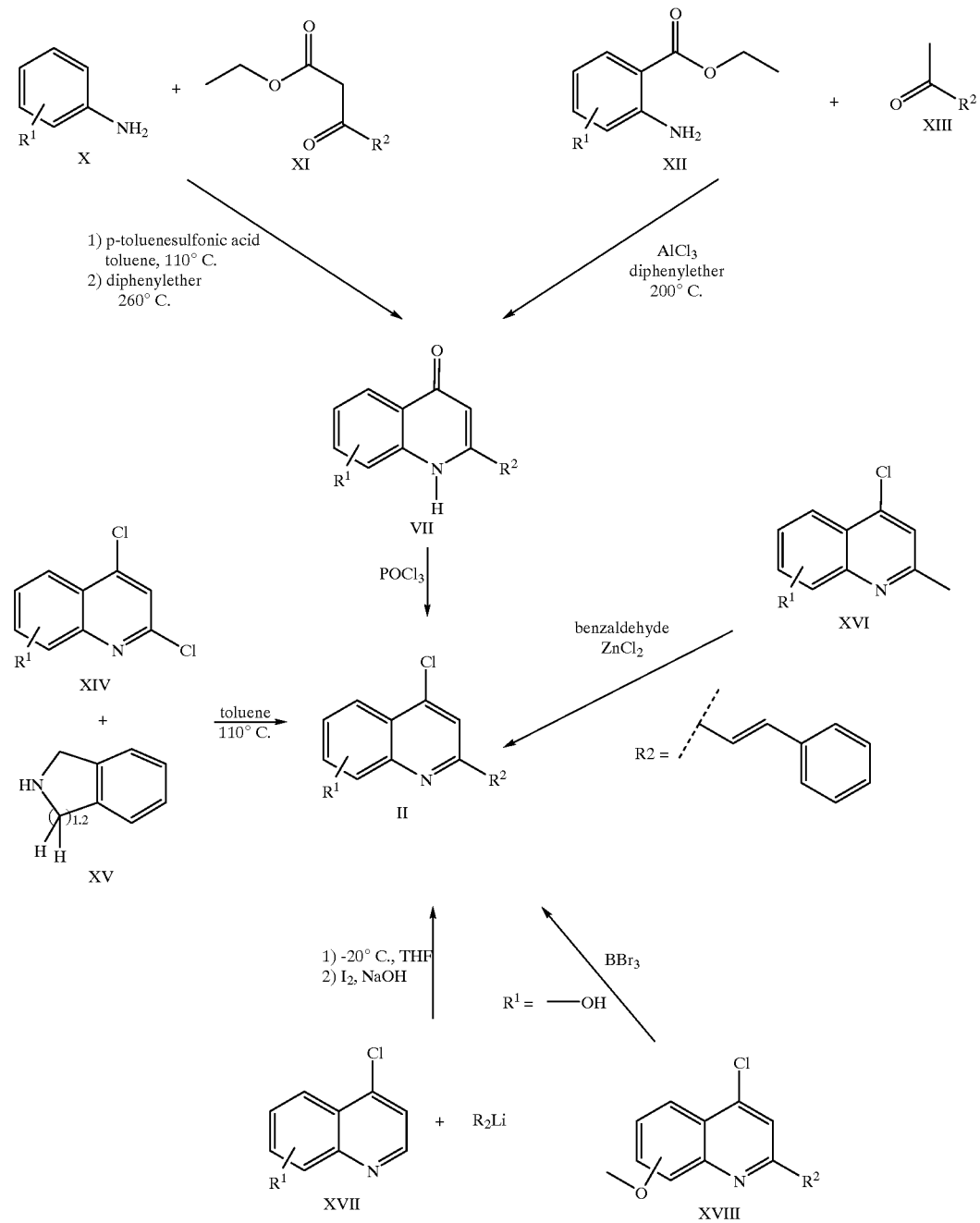

2-Amino-4-chloro-quinoline have been prepared by reacting of 2,4-dichloro-quinoline with a dialkylamine in refluxing toluene. This reaction was found to be completely regioselective (scheme 3).

Preparation of 2-alkyl; 2-aryl or 2-heteroaryl-4-chloro-quinolines (scheme 3):

Known procedures have been used:
- by adding an aryl or heteroaryl lithium to a 4-chloro-2-unsubstituted-quinoline followed by treatment with an oxidant like iodine[1]
- by converting a quinolin-4-one to the corresponding 4-chloro derivative in the presence of a chlorinating agent like phosphorus oxychloride[1]

[1]Field, G. F.; Zally, W. J. (Hoffmann-La Roche, Inc., USA). U.S. Pat. No. 4,560,692

Preparation of 2-styryl-4-chloro-quinolines (scheme 3)

By known procedure has been used reaction of a 2-methyl-4-chloro-quinoline with benzaldehyde.[2]

[2]I. G. Farbenind.; DE 440008

Preparation of hydroxy-4-chloro-quinolines (scheme 3)

By reaction of methoxy substituted-4-chloro-quinoline with $BBr_3$.

Preparation of quinolin-4-ones (scheme 3)

Known procedures have been used
- by condensation of an aniline with a β-ketoester[4] or
- by condensation of derivatives of anthranilic acid and aceto phenones[5].

[4]Hauser, C. R.; Reynolds, G. A.; J. Am. Chem. Soc. 1948,70, 2402; Hauser, C. R.; Murray, J. G.; J. Am. Chem. Soc. 1955,77, 2851.
[5]Jones G.; Quinolines, The Chemistry of Heterocyclic Compounds, Vol 32, Wiley, N.Y., 1977, 181–191, 195–207

Pharmaceutically acceptable salts can be manufactured according to methods which are known per se and familiar to any person skilled in the art. The acid addition salts of compounds of formula I are especially well suited for pharmaceutical use.

In schemes 1–3 are described processes for preparation of compounds of formula 1, starting from known compounds, from commercial products or from compounds, which can be prepared in conventional manner.

The preparation of compounds of formula I are described in more detail in working examples 1–103.

As mentioned earlier, the compounds of formula I and their pharmaceutically usable acid addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the test given hereinafter.

Test method

3H-Ro 25-6981 binding (Ro 25-6981 is [R-(R*, S*)]-a-(4-Hydroxy-phenyl)-b-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10 000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

3H-Ro 25-6981 binding experiments were performed using a Tris-HCl 50 mM, pH 7.4 buffer. For displacement experiments 5 nM of 3H-Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$) with their relative upper and lower 95% confidence limits (RS1, BBN, USA).

The $IC_{50}(\mu M)$ of preferred compounds tested in accordance with the above mentioned methods are in the range of about 0.01–0.15.

In the table below are given some $IC_{50}$ ($\mu M$) for preferred compounds:

| Compound | $IC_{50}$ ($\mu M$) |
| --- | --- |
| (RS)-1-amino-3-(2-p-tolyl-quinolin-4-ylamino)-propan-2-ol hydrochloride | 0.02 |
| (RS)-1-Amino-3-[2-(3,4-dihydro-1H-isoquinolin-2-yl)-quinolin-4-ylamino]-propan-2-ol hydrochloride | 0.03 |
| 2-[2-(5,6,7,8-Tetrahydro-naphthalen-2-yl)-quinolin-4-ylamino]-ethanol hydrochloride | 0.04 |
| (RS)-1-[2-(4-methoxy-phenyl)-quinolin-4-ylamino]-3-methylamino-propan-2-ol hydrochloride | 0.058 |
| (RS)-3-[2-(2,3-dihydro-benzofuran-5-yl)-quinolin-4-ylamino]-propane-1,2-diol hydrochloride | 0.066 |
| 2-{[2-(4-methoxy-phenyl)-quinolin-4-yl]-methyl-amino}-ethanol hydrochloride | 0.13 |

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of about 0.1 mg per dosage to about 1000 mg per day of a compound of formula I although the upper limit can also be exceeded when this is shown to be indicated.

The following examples illustrate the present invention in more detail. However, they are not intended to limit its scope in any manner. All temperatures are given in degree celsius.

EXAMPLE 1

2-[2-(3,4-Dihydro-1H-isoquinolin-2-yl)-quinolin-4-ylaminol-ethanol hydrochloride 4-Chloro-2-(3,4-dihydro-1H-isoquinolin-2-yl)-quinoline (0.5 g, 1.7 mmol) and ethanolamine (0.61 ml, 10.2 mmol) were mixed and heated at 150–160° C. for 16 hours. The reaction mixture was cooled to room temperature and water (20 ml) was added. After decantation of water, the gummy residue was dissolved in ethyl acetate, dried over $Na_2SO_4$ and the solvent was evaporated. The residue was chromatographed over silica gel ($CH_2Cl_2$—MeOH, 9:1 then 4:1) to provide a white foam which was dissolved in MeOH (5 ml). HCl-$Et_2O$ was added to provide 2-[2-(3,4-dihydro-1H-isoquinolin-2-yl)-quinolin-4-ylamino]-ethanol hydrochloride (0.16 g, 27%) as a white solid, m.p. 130–140° C. and MS: m/e=320.3 (M+H+).

Following the general method of example 1 the compounds of example 2 to example 74 were prepared.

EXAMPLE 2

(RS)-1-Amino-3-(2-p-tolyl-quinolin-4-ylamino)-propan-2-ol hydrochloride

The title compound, m.p. 264–272° C. and MS: m/e=308.3 (M+H+), was prepared from 4-chloro-2-p-tolyl-quinoline and 1,3-diamino-2-propanol.

EXAMPLE 3

(RS)-1-Amino-3-[2-(4-methoxy-phenyl)-guinolin-4-ylamino]-propan-2-ol hydrochloride The title compound, m.p. 260–264° C. and MS: m/e=324.3 (M+H+), was prepared from 4-chloro-2-(4-methoxy-phenyl)-quinoline and 1,3-diamino-2-propanol.

EXAMPLE 4

S(+)-1-2-(4-Methoxy-phenyl)-quinolin-4-ylamino]-propan-2-ol-hydrochloride

The title compound, m.p. 226–227° C., $[\alpha]_D^{20}=+18.1°$ (c=0.1, methanol) and MS: m/e=309.2 (M+H+), was prepared from 4-chloro-2-(4-methoxy-phenyl)-quinoline and S(+)-1-amino-2-propanol.

EXAMPLE 5

2-[2-(4-Methoxy-phenyl)-7-methyl-quinolin-4-ylamino]-ethanol hydrochloride

The title compound, m.p. 233–238° C. and MS: m/e=309.2 (M+H+), was prepared from 4-chloro-2-(4-methoxy-phenyl)-7-methyl-quinoline and ethanolamine.

EXAMPLE 6

(S)-1-[2-(4-Methoxy-3-methyl-phenyl)-quinolin-4-ylamino]-propan-2-ol hydrochloride The title compound, m.p. 266–267° C., $[\alpha]_D^{20}=+12.60$ (c=0.29, methanol) and MS: m/e=322 (M+), was prepared from 4-chloro-2-(4-methoxy-3-methyl-phenyl)-quinoline and S(+)-1-amino-2-propanol.

EXAMPLE 7

2-(7-Methyl-2-p-tolyl-quinolin-4-ylamino)-ethanol hydrochloride

The title compound, m.p. 260–263° C. and MS: m/e=293.3 (M+H+), was prepared from 4-chloro-7-methyl-2-p-tolyl-quinoline and ethanolamine.

EXAMPLE 8

(S)-1-[2-(3-Chloro-4-methyl-phenyl)-quinolin-4-ylamino]-propan-2-ol hydrochloride The title compound, m.p. 249–252° C., MS: m/e=326 (M+), was prepared from 4-chloro-2-(3-chloro-4-methyl-phenyl)-quinoline and S(+)-1-amino-2-propanol.

EXAMPLE 9

(RS)-3-[2-(3,4-Dihydro-1H-isoquinolin-2-yl)-quinolin-4-ylamino]-propane-1,2-diol The title compound, MS: m/e=349 (M+), was prepared from 4-chloro-2-(3,4-dihydro-1H-isoquinolin-2-yl)-quinoline and (RS)-3-amino-1,2-propanediol.

EXAMPLE 10

(RS)-1-Amino-3-[2-(3,4-dihydro-1H-isoquinolin-2-yl)-quinolin-4-ylamino]-propan-2-ol hydrochloride The title compound, m.p. 265–275° C., MS: m/e=348 (M+), was prepared from 4-chloro-2-(3,4-dihydro-1H-isoquinolin-2-yl)-quinoline and 1,3-diamino-2-propanol.

EXAMPLE 11

2-[7-Methoxy-2-(4-methoxy-phenyl)-quinolin-4-ylamino]-ethanol hydrochloride

The title compound, m.p. 244–245° C. and MS: m/e=325.3 (M+H+), was prepared from 4-chloro-7-methoxy-2-(4-methoxy-phenyl)-quinoline and ethanolamine.

EXAMPLE 12

(RS)-1-Amino-3-[7-methoxy-2-(4-methoxy-phenyl)-quinolin-4-ylamino]-propan-2-ol hydrochloride The title compound, m.p. 190–205° C. and MS: m/e=353 (M+), was prepared from 4-chloro-7-methoxy-2-(4-methoxy-phenyl)-quinoline and 1,3-diamino-2-propanol.

EXAMPLE 13

(RS)-1-Amino-3-(7-methoxy-2-p-tolyl-quinolin-4-ylamino)-propan-2-ol hydrochloride The title compound, MS: m/e=337 (M+), was prepared from 4-chloro-7-methoxy-2-p-tolyl-quinoline and 1,3-diamino-2-propanol.

EXAMPLE 14

(S)-1-2-(4-Methoxy-phenyl)-7-methyl-quinolin-4-ylamino]-propan-2-ol hydrochloride The title compound, m.p. 189–192° C., MS: m/e=323.3 (M+H$^+$), was prepared from 4-chloro-2-(4-methoxy-phenyl)-7-methyl-quinoline and S(+)-1-amino-2-propanol.

EXAMPLE 15

(E)-(RS)-3-(2-Styryl-quinolin-4-ylamino)-propane-1,2-diol fumarate

The title compound, m.p. 220–222° C. and MS: m/e=321.2 (M+H$^+$), was prepared from (E)-4-Chloro-2-styryl-quinoline and (RS)-3-amino-1,2-propandiol.

EXAMPLE 16

2-(7-Methoxy-2-phenyl-quinolin-4-ylamino)-ethanol hydrochloride

The title compound, m.p. 197° C. and MS: m/e=294 (M$^+$), was prepared from 4-chloro-7-methoxy-2-phenyl-quinoline and ethanolamine.

EXAMPLE 17

2-[2-(4-Methoxy-phenyl)-quinolin-4-ylamino]-ethanol hydrochloride

The title compound, m.p. 211–213° C. and MS: m/e=294 (M$^+$), was prepared from 4-chloro-2-(4-methoxy-phenyl)-quinoline and ethanolamine.

EXAMPLE 18

2-[2-(5,6,7,8-Tetrahydro-naphthalen-2-yl)-quinolin-4-ylamino]-ethanol hydrochloride The title compound, m.p. 250–252° C. and MS: m/e=319.4 (M+H$^+$), was prepared from 4-chloro-2-(5,6,7,8-tetrahydro-naphthalen-2-yl)-quinoline and ethanolamine.

EXAMPLE 19

(S)-1-(7-Methyl-2-p-tolyl-quinolin-4-ylamino)-propan-2-ol hydrochloride

The title compound, m.p. 264–267° C., MS: m/e=307.3 (M+H$^+$), was prepared from 4-chloro-7-methyl-2-p-tolyl-quinoline and S(+)-1-amino-2-propanol.

EXAMPLE 20

(RS)-3-[2-(3-Chloro-4-methyl-phenyl)-quinolin-4-ylamino]-propane-1,2-diol hydrochloride The title compound, m.p. 230–231° C. and MS: m/e=343.1 (M+H$^+$), was prepared from 4-chloro-2-(3-chloro-4-methyl-phenyl)-quinoline and (RS)-3-amino-1,2-propandiol.

EXAMPLE 21

(S)-1-(2-p-Tolyl-quinolin-4-ylamino)-propan-2-ol hydrochloride

The title compound, m.p. 280–281° C., [α]$_D^{20}$=+17.0° (c=0.43, methanol) and MS: m/e=292 (M$^+$), was prepared from 4-chloro-2-p-tolyl-quinoline and S(+)-1-amino-2-propanol.

EXAMPLE 22

(RS)-3-[2-(4-Methoxy-phenyl)-quinolin-4-ylamino]-propane-1,2-diol hydrochloride

The title compound, m.p. 216–218° C. and MS: m/e=324 (M$^+$), was prepared from 4-chloro-2-(4-methoxy-phenyl)-quinoline and (RS)-3-amino-1,2-propandiol.

EXAMPLE 23

(RS)-1-Amino-3-[2-(4-chloro-phenyl)-7-methoxy-quinolin-4-ylamino]-propan-2-ol hydrochloride The title compound, m.p. 269–271° C. and MS: m/e=358.1 (M+H$^+$), was prepared from 4-chloro-2-(4-chloro-phenyl)-7-methoxy-quinoline and 1,3-diamino-2-propanol.

EXAMPLE 24

2-(7-Methoxy-2-p-tolyl-quinolin-4-ylamino)-ethanol hydrochloride

The title compound, m.p. 254–255° C. and MS: m/e=309.2 (M+H$^+$), was prepared from 4-chloro-7-methoxy-2-p-tolyl-quinoline and ethanolamine.

EXAMPLE 25

(S)-2-(3-Chloro-4-methoxy-phenyl)-quinolin-4-ylamino]-propan-2-ol hydrochloride

The title compound, m.p. 249–251° C., MS: m/e=342 (M$^+$), was prepared from 4-chloro-2-(3-chloro-4-methoxy-phenyl)-quinoline and S(+)-1-amino-2-propanol.

EXAMPLE 26

2-(2-p-Tolyl-quinolin-4-ylamino)-ethanol hydrochloride

The title compound, m.p. 274–276° C. and MS: m/e=278 (Me), was prepared from 4-chloro-2-p-tolyl-quinoline and ethanolamine.

EXAMPLE 27

(RS)-3-[2-(3,4-Dimethyl-phenyl)-quinolin-4-ylamino]-propane-1,2-diol hydrochloride The title compound, m.p. 248° C. and MS: m/e=322 (M$^+$), was prepared 4-chloro-2-(3,4-dimethyl-phenyl)-quinoline and (RS)-3-amino-1,2-propandiol.

EXAMPLE 28

(RS)-3-(2-p-Tolyl-quinolin-4-ylamino)-propane-1,2-diol hydrochloride

The title compound, m.p. 255–257° C. and MS: m/e=308 (M$^+$), was prepared from 4-chloro-2-p-tolyl-quinoline and (RS)-3-amino-1,2-propandiol.

EXAMPLE 29

(RS)-1-Amino-3-(7-methoxy-2-phenyl-quinolin-4-ylamino)-propan-2-ol hydrochloride The title compound, m.p. 184–186° C. (and MS: m/e=323 (M$^+$), was prepared from 4-chloro-7-methoxy-2-phenyl-quinoline and 1,3-diamino-2-propanol.

EXAMPLE 30

(RS)-3-[2-(5,6,7,8-Tetrahydro-naphthalen-2-yl)-quinolin-4-ylamino]-propane-1,2-diol hydrochloride The title compound, m.p. 210–230° C. and MS: m/e=348 (M$^+$), was prepared from 4-chloro-2-(5,6,7,8-tetrahydro-naphthalen-2-yl)-quinoline and (RS)-3-amino-1,2-propandiol.

EXAMPLE 31

(S)-1-[2-(2,3-Dihydro-benzofuran-5-yl)-quinolin-4-ylamino]-propan-2-ol hydrochloride The title compound, m.p. 236–242° C., MS: m/e=321.3 (M+H$^+$), was prepared from 4-chloro-2-(2,3-dihydro-benzofuran-5-yl)-quinoline and S(+)-1-amino-2-propanol.

EXAMPLE 32

(RS)-3-[2-(2,3-Dihydro-benzofuran-5-yl)-quinolin-4-ylamino]-propane-1,2-diol hydrochloride The title compound, m.p. 267–270° C. and MS: m/e=336 (M$^+$), was prepared from 4-chloro-2-(2,3-dihydro-benzofuran-5-yl)-quinoline and (RS)-3-amino-1,2-propandiol.

EXAMPLE 33

(S)-1-(7-Methoxy-2-phenyl-quinolin-4-ylamino)-propan-2-ol hydrochloride

The title compound, m.p. 139–141° C., $[\alpha]_D^{20}$=+19.7° (c=0.5, methanol) and MS: m/e=308 (M$^+$), was prepared from 4-chloro-7-methoxy-2-phenyl-quinoline and S(+)-1-amino-2-propanol.

EXAMPLE 34

(RS)-3-[2-(4-Methoxy-3-methyl-phenyl)-quinolin-4-ylamino]-propane-1,2-diol hydrochloride The title compound, m.p. 166–171° C., and MS: m/e=338 (M$^+$), was prepared from 4-chloro-2-(4-methoxy-3-methyl-phenyl)-quinoline and (RS)-3-amino-1,2-propandiol.

EXAMPLE 35

(RS)-3-(7-Methoxy-2-phenyl-quinolin-4-ylamino)-propane-1,2-diol hydrochloride

The title compound, m.p. 218–222° C., and MS: m/e=325.3 (M+H$^+$), was prepared from 4-chloro-7-methoxy-2-phenyl-quinoline and (RS)-3-amino-1,2-propandiol.

EXAMPLE 36

(RS)-3-[2-(3,4-Dichloro-phenyl)-quinolin-4-ylamino]-propane-1,2-diol hydrochloride The title compound, m.p. 234–236° C., and MS: m/e=362 (M$^+$), was prepared from 4-chloro-2-(3,4-dichloro-phenyl)-quinoline and (RS)-3-amino-1,2-propandiol.

EXAMPLE 37

2-[2-(4-Chloro-phenyl)-7-methoxy-quinolin-4-ylamino]-ethanol hydrochloride

The title compound, m.p. 271–272° C., and MS: m/e=328 (M$^+$), was prepared from 4-chloro-2-(4-chloro-phenyl)-7-methoxy-quinoline and ethanolamine.

EXAMPLE 38

(RS)-3-[2-(3-Chloro-4-methoxy-phenyl)-quinolin-4-ylamino]-propane-1,2-diol hydrochloride The title compound, m.p. 205–210° C., and MS: m/e=358 (M$^+$), was prepared from 4-chloro-2-(3-chloro-4-methoxy-phenyl)-quinoline and (RS)-3-amino-1,2-propandiol.

EXAMPLE 39

2-[2-(4-Chloro-phenyl)-quinolin-4-ylamino]-ethanol hydrochloride

The title compound, m.p. 262–264° C., and MS: m/e=299.2 (M+H$^+$), was prepared from 4-chloro-2-(4-chloro-phenyl)-quinoline and ethanolamine.

EXAMPLE 40

(RS)-1-Amino-3-[2-(3,4-dichloro-phenyl)-quinolin-4-ylamino]-propan-2-ol hydrochloride The title compound, m.p. 230–24° C., and MS: m/e=362.1 (M+H$^+$), was prepared from 4-chloro-2-(3,4-dichloro-phenyl)-quinoline and 1,3-diamino-2-propanol.

EXAMPLE 41

2-[2-(3,4-Dichloro-phenyl)-7-methoxy-quinolin-4-ylamino]-ethanol hydrochloride

The title compound, m.p. 268–27° C., and MS: m/e=363.0 (M+H$^+$), was prepared from 4-chloro-2-(3,4-dichloro-phenyl)-7-methoxy-quinoline and ethanolamine.

EXAMPLE 42

(RS)-1-Amino-3-[2-(3,4-dichloro-phenyl)-7-methoxy-quinolin-4-ylamino]-propan-2-ol hydrochloride The title compound, m.p. 230–233° C., and MS: m/e=391 (M$^+$), was prepared from 4-chloro-2-(3,4-dichloro-phenyl)-7-methoxy-quinoline and 1,3-diamino-2-propanol.

EXAMPLE 43

(R)-1-[2-(4-Methoxy-phenyl)-quinolin-4-yl]-pyrrolidin-3-ol hydrochloride

The title compound, m.p. 266–267° C., and MS: m/e=321.3 (M+H$^+$), was prepared from 4-chloro-2-(4-methoxy-phenyl)-quinoline and (R)-3-hydroxypyrrolidine.

EXAMPLE 44

(RS)-1-Amino-3-[[2-(4-chlorophenyl)-4-quinolinyl]amino]-2-propanol dihydrochloride The title compound, m.p. 283–287° C., and MS: m/e=328.2 (M+H$^+$), was prepared from 4-chloro-2-(4-chloro-phenyl)-quinoline and 1,3-diamino-2-propanol.

EXAMPLE 45

(RS)-3-(2-Chroman-6-yl-quinolin-4-ylamino)-propane-1,2-diol hydrochloride

The title compound, MS: m/e=351.3 (M+H'), was prepared from 4-chloro-2-chroman-6-yl-quinoline and (RS)-3-amino-1,2-propandiol.

EXAMPLE 46

2-{[2-(4-Methoxy-phenyl)-quinolin-4-yl]-methyl-amino}-ethanol hydrochloride

The title compound, m.p. 201–204° C., and MS: m/e=309.2 (M+H$^+$), was prepared from 4-chloro-2-(4-methoxy-phenyl)-quinoline and 2-(Methylamino)-ethanol.

EXAMPLE 47

(RS)-1-Amino-3-(2-naphthalen-2-yl-quinolin-4-ylamino)-propan-2-ol hydrochloride

The title compound, m.p. 288–291° C., MS: m/e=343 (M+), was prepared 4-chloro-2-naphthalen-2-yl-quinoline and 1,3-diamino-2-propanol.

EXAMPLE 48

(RS)-3-(2-Indan-5-yl-quinolin-4-ylamino)-propane-1,2-diol hydrochloride

The title compound, m.p. 157–160° C., MS: m/e=334 (M+), was prepared from 4-chloro-2-indan-5-yl-quinoline and (RS)-3-amino-1,2-propandiol.

EXAMPLE 49

2-(7-Methyl-2-phenyl-quinolin-4-ylamino)-ethanol hydrochloride

The title compound, m.p. 234–236° C., and MS: m/e=278 (M+), was prepared from 4-chloro-7-methyl-2-phenyl-quinoline and ethanolamine.

EXAMPLE 50

(R)-{1-[2-(4-Methoxy-phenyl)-quinolin-4-yl]-pyrrolidin-2-yl}-methanol hydrochloride The title compound, m.p. 148–160° C., $[\alpha]_D^{20}$=−62.6° (c=0.51, methanol) and MS: m/e=334 (M+), was prepared from 4-chloro-2-(4-methoxy-phenyl)-quinoline and D-prolinol.

EXAMPLE 51

2-(8-Methoxy-2-phenyl-quinolin-4-ylamino)-ethanol hydrochloride

The title compound, m.p. 205–209° C., and MS: m/e=295.3 (M+H+), was prepared from 4-chloro-8-methoxy-2-phenyl-quinoline and ethanolamine.

EXAMPLE 52

2-[2-(3,4-Dichloro-phenyl)-quinolin-4-ylamino]-ethanol hydrochloride

The title compound, m.p. 256–25° C., and MS: m/e=333.1 (M+H+), was prepared from 4-chloro-2-(3,4-dichloro-phenyl)-quinoline and ethanolamine.

EXAMPLE 53

(RS)-1-Dimethylamino-3-[2-(4-methoxy-phenyl)-quinolin-4-ylaminol-propan-2-ol hydrochloride The title compound, m.p. 226–228° C., and MS: m/e=352.3 (M+H+), was prepared from 4-chloro-2-(4-methoxy-phenyl)-quinoline and (RS)-1-amino-3-dimethylamino-propan-2-ol.

(RS)-1-amino-3-dimethylamino-propan-2-ol is a known compound and has been prepared as described in the following reference: I. G. Farbenind. DE 479354.

EXAMPLE 54

(RS)-3-[2-(1,3-Dihydro-isoindol-2-yl)-quinolin-4-ylamino]-propane-1,2-diol hydrochloride The title compound, m.p. 295–301° C., and MS: m/e=336.2 (M+H+), was prepared from 4-chloro-2-(1,3-dihydro-isoindol-2-yl)-quinoline and (RS)-3-amino-1,2-propandiol.

EXAMPLE 55

(RS)-1-Amino-3-(2-phenyl-quinolin-4-ylamino)-propan-2-ol hydrochloride

The title compound, m.p. 291–294° C., MS: m/e=294.3 (M+H+), was prepared from 4-chloro-2-phenyl-quinoline and 1,3-diamino-2-propanol.

EXAMPLE 56

(RS)-3-[2-(4-Trifluoromethyl-phenyl)-quinolin-4-ylamino]-propane-1,2-diol hydrochloride The title compound, m.p. 243–247° C., and MS: m/e=362 (M+), was prepared from 4-chloro-2-(4-trifluoromethyl-phenyl)-quinoline and (RS)-3-amino-1,2-propandiol.

EXAMPLE 57

(S)-1-(2-Phenyl-quinolin-4-ylamino)-propan-2-ol hydrochloride

The title compound, m.p. 251–252° C., $[\alpha]_D^{20}$=+20.3° (c=0.43, methanol) and MS: m/e=278 (M+), was prepared from 4-chloro-2-phenyl-quinoline and S(+)-1-amino-2-propanol.

EXAMPLE 58

(RS)- and (SR)-3-[2-[(RS)-1,2,3,4-Tetrahydro-naphthalen-2-yl]-quinolin-4-ylamino]-propane-1,2-diol hydrochloride The title compound, m.p. 212–218° C., and MS: m/e=348 (M+), was prepared from (RS)-4-chloro-2-(1,2,3,4-tetrahydro-naphthalen-2-yl)-quinoline and (RS)-3-amino-1,2-propandiol.

EXAMPLE 59

(RS)-3-[2-(4-Chloro-phenyl)-quinolin-4-ylaminol-propane-1,2-diol hydrochloride

The title compound, m.p. 232–236° C., and MS: m/e=328 (M+), was prepared from 4-chloro-2-(4-chloro-phenyl)-quinoline and (RS)-3-amino-1,2-propandiol.

EXAMPLE 60

2-(2-Phenyl-quinolin-4-ylamino)-ethanol hydrochloride

The title compound, m.p. 258–260° C., MS: m/e=264 (M+), was prepared from 4-chloro-2-phenyl-quinoline and ethanolamine.

EXAMPLE 61

(RS)-3-(8-Methoxy-2-phenyl-quinolin-4-ylamino)-propane-1,2-diol hydrochloride

The title compound, m.p. 110–116° C., and MS: m/e=325.3 (M+H+), was prepared from 4-chloro-8-methoxy-2-phenyl-quinoline and (RS)-3-amino-1,2-propandiol.

EXAMPLE 62

(RS)-3-(7-Hydroxy-2-phenyl-quinolin-4-ylamino)-propane-1,2-diol hydrochloride

The title compound, m.p. 267–268° C., and MS: m/e=310 (M+), was prepared from 4-chloro-2-phenyl-quinolin-7-ol and (RS)-3-amino-1,2-propandiol.

EXAMPLE 63

(RS)-3-(2-Benzofuran-2-yl-quinolin-4-ylamino)-propane-1,2-diol hydrochloride

The title compound, m.p. 263–265° C., and MS: m/e=335.2(M+H$^+$), was prepared from 2-benzofuran-2-yl-4-chloro-quinoline and (RS)-3-amino-1,2-propandiol.

EXAMPLE 64

(RS)-3-(2-m-Tolyl-quinolin-4-ylamino)-propane-1,2-diol hydrochloride

The title compound, m.p. 208–215° C., and MS: m/e=309.2 (M+H$^+$), was prepared from 4-chloro-2-m-tolyl-quinoline and (RS)-3-amino-1,2-propandiol.

EXAMPLE 65

(RS)-1-Amino-3-[[2-(4-chlorophenyl)-4-quinolinyl]amino]-2-propanol

The title compound, m.p. 283–287° C. and MS: m/e=328.2 (M+H$^+$), was prepared from 4-chloro-2-(4-chlorophenyl)-quinoline and 1,3-diamino-2-propanol.

EXAMPLE 66

(S)-1-[2-(4-Methoxy-phenyl)-quinolin-4-yl]-pyrrolidin-3-ol hydrochloride

The title compound, m.p. 270–271° C., MS: m/e=321.3 (M+H$^+$), was prepared 4-chloro-2-(4-methoxy-phenyl)-quinoline and (S)-3-hydroxypyrrolidine.

EXAMPLE 67

(RS)-3-2-(4-Dimethylamino-phenyl)-quinolin-4-ylamino]-propane-1,2-diol hydrochloride The title compound, m.p. 250–260 ° C., and MS: m/e=338.2 (M+H$^+$), was prepared from [4-(4-chloro-quinolin-2-yl)-phenyl]-dimethyl-amine and (RS)-3-amino-1,2-propandiol.

EXAMPLE 68

(RS)-3-(6-Hydroxy-2-phenyl-quinolin-4-ylamino)-propane-1,2-diol hydrochloride

The title compound, m.p. 303–304° C., and MS: m/e=310 (M$^+$), was prepared from 4-chloro-2-phenyl-quinolin-6-ol and (RS)-3-amino-1,2-propandiol.

EXAMPLE 69

(RS)-3-(2-Phenyl-quinolin-4-ylamino)-propane-1,2-diol hydrochloride

The title compound, m.p. 225–227° C., and MS: m/e=295.3 (M+H$^+$), was prepared from 4-chloro-2-phenyl-quinolin and (RS)-3-amino-1,2-propandiol.

EXAMPLE 70

(RS)-1-(2-Phenyl-quinolin-4-ylamino)-propan-2-ol hydrochloride

The title compound, m.p. 251–253° C., and MS: m/e=279.2 (M+H$^+$), was prepared from 4-chloro-2-phenyl-quinolin and (RS)-1-amino-2-propanol.

EXAMPLE 71

R-(+)-1-(2-Phenyl-quinolin-4-yl)-pyrrolidin-3-ol-hydrochloride

The title compound, m.p. 291–293, $[\alpha]_D^{20}$=+54.4° (c=0.11, methanol) and MS: m/e=291.2 (M+H$^+$), was prepared from 4-chloro-2-phenyl-quinolin and (R)-3-hydroxypyrrolidine.

EXAMPLE 72

(RS)-3-(2-Benzo[b]thiophen-2-yl-quinolin-4-ylamino)-propane-1,2-diol hydrochloride The title compound, m.p. 253–255° C., and MS: m/e=386 (M$^+$), was prepared from 2-benzo[b]thiophen-2-yl-4-chloro-quinoline and (RS)-3-amino-1,2-propandiol.

EXAMPLE 73

(RS)-3-(7-Chloro-2-phenyl-quinolin-4-ylamino)-propane-1,2-diol hydrochloride

The title compound, m.p. 234–236° C., and MS: m/e=328 (M$^+$), was prepared from 4,7-dichloro-2-phenyl-quinoline and (RS)-3-amino-1,2-propandiol.

EXAMPLE 74

(RS)-1-[2-(4-Methoxy-phenyl)-quinolin-4-ylamino]-3-piperidin-1-yl-propan-2-ol hydrochloride The title compound, m.p. 269–272° C., and MS: m/e=392.3 (M+H$^+$), was prepared from 4-chloro-2-(4-methoxy-phenyl)-quinoline and (RS)-1-amino-3-piperidin-1-yl-propan-2-ol.

(RS)-1-Amino-3-piperidin-1-yl-propan-2-ol is a known compound and has been prepared as described in the following reference: I. G. Farbenind.; DE 479354.

EXAMPLE 75

(RS)-3-(2-Phenethyl-quinolin-4-ylamino)-propane-1,2-diol hydrochloride (E)-(RS)-3-(2-Styryl-quinolin-4-ylamino)-propane-1,2-diol (0.23 g, 0.718 mmol) was dissolved in MeOH (25 ml) and acidified with HCl/Et$_2$O. The reaction mixture was refluxed for 2 hours in the presence of 10% Pd/C (0.02 g) under an atmospheric pressure of hydrogen. The mixture was cooled to room temperature, the catalyst was filtered, and the filtrate was concentrated. Addition of EtOH provided (RS)-3-(2-phenethyl-quinolin-4-ylamino)-propane-1,2-diol hydrochloride (0.075 g, 29%) as a light yellow solid, m. p. 143–145° C., MS: m/e=323.3 (M+H$^+$).

Following the method of example 75 the compound of example 76 was prepared.

EXAMPLE 76

(RS)-3-(6-Amino-2-phenyl-quinolin-4-ylamino)-propane-1,2-diol hydrochloride

The title compound, m.p. 239–241° C., MS: m/e=309 (M$^+$), was prepared from (RS)-3-(6-nitro-2-phenyl-quinolin-4-ylamino)-propane-1,2-diol hydrochloride.

(RS)-3-(6-Nitro-2-phenyl-quinolin-4-ylamino)-propane-1,2-diol hydrochloride was prepared according to the general procedure described in example 1 from 4-chloro-6-nitro-2phenyl-quinoline and (RS)-3-amino-1,2-propandiol.

EXAMPLE 77

(RS)-1-[2-(4-Methoxy-phenyl)-quinolin-4-ylamino]-3-methylamino-propan-2-ol hydrochloride (RS)-5-{[2-(4-Methoxy-phenyl)-quinolin-4-ylamino]-methyl}-oxazolidin-2-one (0.1 g, 0.286 mmol) in THF (3 ml) was added dropwise to a suspension of LiAlH$_4$ (0.054 g, 1.43 mmol) in THF at 0° C. Reaction mixture was refluxed for 1 hour, cooled to 0° C., treated successively with H$_2$O (50 µl), 5N NaOH (50 µl), H$_2$O (150 µl), filtered, and concentrated. The residue was chromatographed over silica gel (CH$_2$Cl$_2$—MeOH, 9:1 then 4:1+1% aqueous NH$_3$) to provide an oil which was dissolved in MeOH. HCl-Et$_2$O was added to provide (RS)-1-[2-(4-methoxy-phenyl)-quinolin-4-ylamino]-3-methylamino-propan-2-ol hydrochloride (0.085 g, 72%) as a white foam, MS: m/e=337 (M$^+$).

Following the general method of Example 77, the compounds of Example 78 to Example 82 were prepared.

EXAMPLE 78

(RS)-1-(7-Methoxy-2-p-tolyl-quinolin-4-ylamino)-3-methylamino-propan-2-ol hydrochloride The title compound, MS: m/e=352.3 (M+H$^+$), was prepared from (RS)-5-[(7-methoxy-2-p-tolyl-quinolin-4-ylamino)-methyl]-oxazolidin-2-one.

EXAMPLE 79

(RS)-1-[2-(4-Chloro-phenyl)-7-methoxy-quinolin-4-ylamino]-3-methylamino-propan-2-ol hydrochloride The title compound, MS: m/e=372.2 (M+H$^+$), was prepared from (RS)-5-{[2-(4-chloro-phenyl)-7-methoxy-quinolin-4-ylamino]-methyl}-oxazolidin-2-one.

EXAMPLE 80

(RS)-1-Methylamino-3-(2-phenyl-quinolin-4-ylamino)-propan-2-ol hydrochloride

The title compound, m.p. 256–259° C. MS: m/e=307 (M$^+$), was prepared from (RS)-5-[(2-phenyl-quinolin-4-ylamino)-methyl]-oxazolidin-2-one.

EXAMPLE 81

(RS)-1-Phenethylamino-3-(2-phenyl-quinolin-4-ylamino)-propan-2-ol

The title compound, NIS: m/e=398 (M+H$^+$), was prepared from (RS)-N-[2-hydroxy-3-(2-phenyl-quinolin-4-ylamino)-propyl]-2-phenyl-acetamide.

EXAMPLE 82

(RS)-1-(3-Phenyl-propylamino)-3-(2-phenyl-quinolin-4-ylamino)-propan-2-ol hydrochloride The title compound, MS: m/e=412.3 (M+H$^+$), was prepared from (RS)-N-[2-hydroxy-3-(2-phenyl-quinolin-4-ylamino)-propyl]-3-phenyl-propionamide.

EXAMPLE 83

(RS)-1-(7-Methoxy-2-phenyl-quinolin-4-yloxy)-3-methylamino-propan-2-ol hydrochloride (RS)-7-Methoxy-4-oxiranylmethoxy-2-phenyl-quinoline (0.2 g, 0.65 mmol) in MeOH (4 ml) was refluxed for 1.2 hour in the presence of a 33% solution of methylamine in EtOH (0.4 ml, 3.3 mmol). The reaction mixture was concentrated and the residue was chromatographed over silica gel (CH$_2$Cl$_2$—MeOH, 9:1 then 4:1+1% aqueous NH$_3$) to provide a foam which was dissolved in MeOH. HCl-Et$_2$O was added to provide (RS)-1-(7-methoxy-2-phenyl-quinolin-4-yloxy)-3-methylamino-propan-2-ol hydrochloride (0.120 g, 45%) as a white solide, m. p. 175–185 ° C., MS: m/e=338 (M$^+$).

Following the general method of example 83 the compounds of example 84 to example 95 were prepared.

EXAMPLE 84

(RS)-1-Amino-3-(2-phenyl-quinolin-4-yloxy)-propan-2-ol hydrochloride

The title compound, m. p. 175–178° C., MS: m/e=294 (M$^+$), was prepared from (RS)-4-oxiranylmethoxy-2-phenyl-quinoline and a 25% solution of NH$_3$ in H$_2$O.

EXAMPLE 85

(RS)-1-Isopropylamino-3-(2-phenyl-quinolin-4-yloxy)-propan-2-ol

The title compound, m. p. 109–111° C., MS: m/e=337.2 (M+H$^+$), was prepared from (RS)-4-oxiranylmethoxy-2-phenyl-quinoline and isopropylamine.

EXAMPLE 86

(RS)-1-Cyclopentylamino-3-(2-phenyl-quinolin-4-yloxy)-propan-2-ol hydrochloride

The title compound, m. p. 109–111° C., MS: m/e=363.2 (M+H$^+$), was prepared from (RS)-4-oxiranylmethoxy-2-phenyl-quinoline and cyclopentylamine.

EXAMPLE 87

(RS)-1-Isopropylamino-3-(7-methoxy-2-phenyl-quinolin-4-yloxy)-propan-2-ol hydrochloride The title compound, m. p. 115–125° C., MS: m/e=366 (M$^+$), was prepared from (RS)-7-methoxy-4-oxiranylmethoxy-2-phenyl-quinoline and isopropylamine.

EXAMPLE 88

(RS)-1-Methylamino-3-(2-p-tolyl-quinolin-4-yloxy)-propan-2-ol hydrochloride

The title compound, m. p. 203–208° C., MS: m/e=322 (Me), was prepared from (RS)-4-oxiranylmethoxy-2-p-tolyl-quinoline and a 33% solution of methylamine in EtOH.

EXAMPLE 89

(RS)-1-Cyclobutylamino-3-(2-phenyl-quinolin-4-yloxy)-propan-2-ol hydrochloride

The title compound, m. p. 190–195° C., MS: m/e=349.4 (M+H$^+$), was prepared from (RS)-4-oxiranylmethoxy-2-phenyl-quinoline and cyclobutylamine.

EXAMPLE 90

(RS)-1-[2-(4-Methoxy-phenyl)-quinolin-4-yloxy]-3-methylamino-propan-2-ol hydrochloride The title compound, m. p. 230–232° C., MS: m/e=338 (M$^+$), was prepared from (RS)-2-(4-methoxy-phenyl)-4- oxiranylmethoxy-quinoline and a 33% solution of methylamine in EtOH.

EXAMPLE 91

1-(6-Fluoro-2-phenyl-quinolin-4-yloxy)-3-methylamino-propan-2-ol hydrochloride

The title compound, m. p. 218–219° C., MS: m/e=326 (M+), was prepared from (RS)-6-fluoro-4-oxiranylmethoxy-2-phenyl-quinoline and a 33% solution of methylamine in EtOH.

EXAMPLE 92

(RS)-(3-Morpholin-4-yl-propylamino)-3-(2-phenyl-quinolin-4-yloxy)-propan-2-ol hydrochloride The title compound, m. p. 151–154° C., MS: m/e=422.4 (M+H+), was prepared from (RS)-4-oxiranylmethoxy-2-phenyl-quinoline and 4-(3-aminopropyl)-morpholine.

EXAMPLE 93

(RS )-1-Ethylamino-3-(2-phenyl-quinolin-4-yloxy)-propan-2-ol hydrochloride

The title compound, m. p. 170–174° C., MS: m/e=323.3 (M+H+), was prepared from (RS)-4-oxiranylmethoxy-2-phenyl-quinoline and ethylamine.

EXAMPLE 94

(RS)-1-Cyclopropylamino-3-(2-phenyl-quinolin-4-yloxy)-propan-2-ol hydrochloride

The title compound, m. p. 145–152° C., MS: m/e=334 (M+H+), was prepared from (RS)-4-oxiranylmethoxy-2-phenyl-quinoline and cyclopropylamine.

EXAMPLE 95

(RS)-1-Butylamino-3-(2-phenyl-quinolin-4-yloxy)-propan-2-ol hydrochloride

The title compound, MS: m/e=351 (M+H+), was prepared from (RS)-4-oxiranylmethoxy-2-phenyl-quinoline and n-butylamine.

EXAMPLE 96

(RS)-1-Methylamino-3-(7-methyl-2-phenyl-quinolin-4-yloxy)-propan-2-ol hydrochloride To a 0° C. suspension of NaH (0.11 g, 2.5 mmol, 55% in mineral oil) in DMF (3 ml) was added dropwise a DMF solution (3 ml) of a mixture of (2RS,5RS) and (2RS,5SR) (3-methyl-2-phenyl-oxazolidin-5-yl)-methanol (0.46 g, 2.4 mmol) in DMF (3 ml). After 15 min. at 0° C. and 2 hours at room temperature, reaction mixture was cooled to 0° C. and treated with a solution of 4-chloro-7-methyl-2-phenyl-quinoline (0.3 g, 1.2 mmol) in DMF (3 ml). After 5 min. at 0° C. and 21 hours at room temperature, the reaction mixture was cooled to 0° C., quenched with $H_2O$ (0.5 ml), and concentrated. The residue was treated with 1N HCl (6 ml). The so obtained yellow aqueous solution was extracted with $CH_2Cl_2$ (3×20 ml). Organic phases were washed with 1N HCl (2×10 ml). Combined aqueous phases were basified to pH 11 with 2N NaOH, and extracted with $CH_2Cl_2$ (3×20 ml). Combined organic phases were dried over $Na_2SO_4$ and concentrated. The residue was crystallized with $Et_2O$ to provide after filtration 95 mg of a white solid which was dissolved in MeOH. HCl-$Et_2O$ was added to provide (RS)-1-methylamino-3-(7-methyl-2-phenyl-quinolin-4-yloxy)-propan-2-ol hydrochloride (0.075 g, 16%) as a white solid, MS: m/e=323.3 (M+H+).

Following the general method of Example 96 the compounds of Example 97 to Example 103 were prepared.

EXAMPLE 97

(RS)-1-(7-Methoxy-2-p-tolyl-quinolin-4-yloxy)-3-methylamino-propan-2-ol hydrochloride The title compound m. p. 240° C., MS: m/e=352 (M+), was prepared from 4-chloro-7-methoxy-2-p-tolyl-quinoline.

EXAMPLE 98

(RS)-1-[7-Methoxy-2-(4-methoxy-phenyl)-quinolin-4-yloxy]-3-methylamino-propan-2-ol hydrochloride The title compound m. p. 245° C., MS: m/e=368 (M+), was prepared from 4-chloro-7-methoxy-2-(4-methoxy-phenyl)-quinoline.

EXAMPLE 99

(RS)-1-[2-(4-Methoxy-phenyl)-7-methyl-quinolin-4-yloxy]-3-methylamino-propan-2-ol The title compound m. p. 140–142° C., MS: m/e=353.3 (M+H+), was prepared from 4-chloro-2-(4-methoxy-phenyl)-7-methyl-quinoline.

EXAMPLE 100

(RS)-1-Methylamino-3-(7-methyl-2-p-tolyl-quinolin-4-yloxy)-propan-2-ol

The title compound m. p. 146–150° C., MS: m/e=337.2 (M+H+), was prepared from 4-chloro-7-methyl-2-p-tolyl-quinoline.

EXAMPLE 101

(RS)-1-[2-(3,4-Dihydro-1H-isoquinolin-2-yl)-quinolin-4-yloxy]-3-methylamino-propan-2-ol hydrochloride The title compound MS: m/e=364.2 (M+H+), was prepared from 4-chloro-2-(3,4-dihydro-1H-isoquinolin-2-yl)-quinoline.

EXAMPLE 102

(RS)-1-(7-Chloro-2-phenyl-quinolin-4-yloxy)-3-methylamino-propan-2-ol hydrochloride The title compound m. p. 192–193° C., MS: m/e=343.2 (M+H+), was prepared from 4,7-dichloro-2-phenyl-quinoline.

EXAMPLE 103

(RS)-1-Methylamino-3-(2-thiophen-3-yl-quinolin-4-yloxy)-propan-2-ol hydrochloride The title compound m. p. 236–238° C. MS: m/e=315.2 (M+H+), was prepared from 4-chloro-2-thiophen-3-yl-quinoline.

Preparation of Intermediates

Preparation of Oxazolidin-2-ones, Precursors of Examples 77–80

EXAMPLE 104

(RS)-5-{[2-(4-Methoxy-phenyl)-quinolin-4-ylamino]-methyl}-oxazolidin-2-one

To a 0° C. solution of (RS)-1-amino-3-[2-(4-methoxy-phenyl)-quinolin-4-ylamino]-propan-2-ol (0.139 g) 0.429 mmol) in DMF (2.5 ml) was added dropwise a solution of 1,1-carbonyldiimidazole (0.076 g, 0.472 mmol) in DMF (1 ml). After 20 min. at 0° C., and 1.5 hours at 60° C., the reaction mixture was cooled to room temperature and concentrated. Addition of $H_2O$ provided (RS)-5-{[2-(4-methoxy-phenyl)-quinolin-4-ylamino]-methyl}-oxazolidin-2-one (0.110 g, 73%) as yellowish solid, MS: m/e=349 ($M^+$).

Following the general method of Example 104, the compounds of Example 105 to Example 107 were prepared.

EXAMPLE 105

(RS)-5-[(7-Methoxy-2-p-tolyl-quinolin-4-ylamino)-methyl -oxazolidin-2-one

The title compound, MS: m/e=364.1 ($M+H^+$), was prepared from (RS)-1-amino-3-(7-methoxy-2-p-tolyl-quinolin-4-ylamino)-propan-2-ol.

EXAMPLE 106

(RS)-5-{[2-(4-Chloro-phenyl )-7-methoxy-quinolin-4-ylamino]-methyl}-oxazolidin-2-one The title compound, MS: m/e=383 ($M^+$), was prepared from (RS)-1-amino-3-[2-(4-chloro-phenyl)-7-methoxy-quinolin-4-ylamino]-propan-2-ol.

EXAMPLE 107

(RS)-5-[(2-Phenyl-quinolin-4-ylamino)-methyl]-oxazolidin-2-one

The title compound, MS: m/e=320.3 ($M+H^+$), was prepared from (RS)-1-amino-3-(2-phenyl-quinolin-4-ylamino)-propan-2-ol.

Preparation of the Amides, Precursors of Examples 81–82

EXAMPLE 108

(RS)-N-[2-Hydroxy-3-(2-phenyl-quinolin-4-ylamino)-propyl]-2-phenyl-acetamide hydrochloride To a room temperature solution of (RS)-1-amino-3-(2-phenyl-quinolin-4-ylamino)-propan-2-ol (0.293 g, 1 mmol) and triethylamine (0.42 ml,3 mmol) in dioxane (6 ml) was added a solution of phenylacetylchloride (0.198 ml, 1.5 mmol) in dioxane (1 ml). After stirring for 3 hours at room temperature, the reaction mixture was quenched with $H_2O$ and 1N NaOH. The aqueous phase was extracted with $CH_2Cl_2$ (5×10 ml). The combined organic phases were dried over $Na_2SO_4$, concentrated and chromatographed over silica gel ($CH_2Cl_2$—MeOH, 19:1 then 9:1) to provide a yellow oil which was dissolved in MeOH. HCl-$Et_2O$ was added to provide (RS)-N-[2-hydroxy-3-(2-phenyl-quinolin-4-ylamino)-propyl]-2-phenyl-acetamide hydrochloride (0.113 g, 25%) as a light yellow foam, MS: m/e=412.3 ($M+H^+$).

Following the general method of Example 108, the compound of Example 109 was prepared.

EXAMPLE 109

(RS)-N-[2-Hydroxy-3-(2-phenyl-quinolin-4-ylamino)-propyl]-3-phenyl-propionamide

The title compound, MS: m/e=426.4 ($M+H^+$), was prepared from (RS)-1-amino-3-(2-phenyl-quinolin-4-ylamino)-propan-2-ol.

Preparation of the Epoxides, Precursors of Examples 83–95

EXAMPLE 110

(RS)-7-Methoxy-4-oxiranylmethoxy-2-phenyl-quinoline

To a solution of 7-methoxy-2-phenyl-1H-quinolin-4-one (1.5 g, 6 mmol) in DMF (11 ml) were added successively $K_2CO_3$ (1.66 g, 12 mmol) and (RS)-epichlorohydrin (1.9 ml, 24 mmol). The reaction mixture was stirred at 65° C. for 3 hours, then cooled to room temperature and diluted with $CH_2Cl_2$ (25 ml). Solid was filtrated, and filtrate was concentrated. The residue was chromatographed over silica gel (hexane-ethyl acetate, 4:1) to provide (RS)-7-methoxy-4-oxiranylmethoxy-2-phenyl-quinoline (1.05 g, 57%) as a colorless oil, MS: m/e=307 ($M^+$).

Following the general method of example 110, the compounds of example 111 to 114 were prepared.

EXAMPLE 111

(RS)-4-Oxiranylmethoxy-2-phenyl-quinoline

The title compound, MS: m/e=277 ($M^+$), was prepared from 2-phenyl-1H-quinolin-4-one.

EXAMPLE 112

(RS)-4-Oxiranylmethoxy-2-p-tolyl-quinoline

The title compound, m. p. 100–102° C., MS: m/e=292.2 ($M+H^+$), was prepared from 2-p-tolyl-1 H-quinolin-4-one.

EXAMPLE 113

(RS)-2-(4-Methoxy-phenyl)-4-oxiranylmethoxy-quinoline

The title compound, m. p. 100–106° C., MS: m/e 307 ($M^+$), was prepared from 2-(4-methoxy-phenyl)-1H-quinolin-4-one.

EXAMPLE 114

(RS)-6-Fluoro-4-oxiranylmethoxy-2-phenyl-quinoline

The title compound, m. p. 118–120° C., MS: m/e=295.9 ($M^+$), was from 6-fluoro-2-phenyl-1H-quinolin-4-one.

Preparation of 4- and 2-chloro-quinolines, Precursors of Examples 1–74 and 96–103 a) Preparation of the 2-amino-4-chloro-quinolines and 2-chloro-4-amino-quinolines

EXAMPLE 115

4-Chloro-2-(3,4-dihydro-1H-isoquinolin-2-yl)-quinoline

A solution of 2,4-dichloroquinoline (0.2 g, 1 mmol) and 1,2,3,4-tetrahydroisoquinoline (0.282 ml, 2.2 mmol) in toluene (2 ml) was refluxed during 18 hours then cooled to room temperature. The reaction mixture was diluted with $CH_2Cl_2$ and quenched with a saturated solution of $NaHCO_3$. Aqueous phase was extracted with $CH_2Cl_2$ (2×). Combined organic phases were washed with $H_2O$, dried over $NaSO_4$, and concentrated. The residue was chromatographed over silica gel (hexane-ethyl acetate, 97:3) to provide 4-chloro-2-(3,4-dihydro-1H-isoquinolin-2-yl)-quinoline (0.235 g, 79%) as a yellow oil, MS: m/e=295.3 (M+H$^+$).

Following the general method of example 15 the compound of example 116 was prepared.

EXAMPLE 116

4-Chloro-2-(1,3-dihydro-isoindol-2-yl)-quinoline

The title compound, m. p. 172–173° C., MS: m/e=281.1 (M+H$^+$), was prepared from 2,3-dihydro-1H-isoindole.

EXAMPLE 117

2-Chloro-4-(3,4-dihydro-1H-isoquinolin-2-yl)-quinoline

A mixture of 2,4-quinolinediol (1 g, 6.2 mmol) and 1,2,3,4-tetrahydroisoquinoline (1.57 ml, 12.4 mmol) was heated overnight under argon at 200° C. Reaction mixture was cooled to room temperature, diluted with MeOH, stirred for 30 min. and filtered. The solid obtained was refluxed overnight in the presence of POCl$_3$ (3 ml). The reaction mixture was cooled to room temperature and poured into a 0° C. stirring mixture of 5N NaOH (50 ml) and CH$_2$Cl$_2$ (50 ml). After 15 min., aqueous phase was extracted with CH$_2$Cl$_2$ (2×), combined organic phases were washed with H$_2$O, dried over Na$_2$SO$_4$ and concentrated. The residue was chromatographed over silica gel (hexane-ethyl acetate, 97:3 then 9:1) to provide 2-chloro-4-(3,4-dihydro-1H-isoquinolin-2-yl)-quinoline (0.1 g, 5%) as a colorless oil, MS: m/e=295.3 (M+H$^+$).

4-Chloro-quinolin-2-ylamine, precursor of example 111, is a known compound and has been prepared as described in the following, reference: R. Hardman, M. W. Partridge, J. C. S., 1958, 614.

b) Preparation of 2-unsubstituted; 2-styryl; 2-alkyl; 2-aryl or 2-heteroaryl-4-chloro-quinolines (E)-4-Chloro-2-styryl-quinoline, precursor of example 15, is a known compound and has been prepared as described in the following reference: I. G. Farbenind.; DE 440008.

Preparation of hydroxylated-4-chloro-quinolines

4-Chloro-quinolin-6-ol is a known compound and has been prepared as described in the following reference: C. Ramsey; J. Am. Chem. Soc.; 69; 1947; 1659–1660

EXAMPLE 118

4-Chloro-2-phenyl-quinolin-6-ol

To a −78° C. solution of 4-chloro-6-methoxy-2-phenyl-quinoline (1.0 g, 3.7 mmol) in CH$_2$Cl$_2$ (25 ml) was added dropwise BBr$_3$ (11.1 ml, 11.1 mmol, 1M in CH$_2$Cl$_2$). Reaction mixture was then allowed to warm to room temperature. After 4.5 hours, mixture was cooled to −10° C. and quenched slowly with a saturated solution of NaHCO$_3$ (70 ml). The aqueous phase was extracted with ethyl acetate (3×100 ml). Combined organic phases were dried over Na$_2$SO$_4$ and concentrated. The solid residue was refluxed during 1 hour in ethyl acetate (30 ml), cooled to room temperature, and filtered. Filtrate was concentrated and chromatographed over silica gel (hexane-ethyl acetate, 4:1) to provide 4-chloro-2-phenyl-quinolin-6-ol (0.375 g, 40%) as a yellow solid, m. p. 180–181° C., MS: m/e=255 (M$^+$).

Following the general method of Example 118, the compound of Example 119 was prepared.

EXAMPLE 119

4-Chloro-2-phenyl-quinolin-7-ol

The title compound, m. p. 190–192° C., MS: m/e=255 (M+H$^+$), was prepared from 4-chloro-7-methoxy-2-phenyl-quinoline Preparation of 4-chloro-quinolines by Reaction of an Aryl Lithium on a 4-chloro-2-unsubstituted Quinoline

EXAMPLE 120

4-Chloro-2-m-tolyl-quinoline

To a −25° C. solution of 3-bromo-tolulene (2.1 ml, 17.4 mmol) in Et$_2$O (20 ml) was added dropwise nBuLi (13.4 ml, 21.4 mmol, 1.6 M in hexane). After 30 min. stirring at −20° C. and 30 min. at 0° C., reaction mixture was cooled to −20° C. A suspension of 4-chloroquinoline (2.5 g, 15.3 mmol) in Et$_2$O (15 ml) was added slowly (15 min.). After 10 min. at −20° C., and 20 min. at 10° C., reaction mixture was quenched slowly with H$_2$O (4 ml). I$_2$ (3.9 g, 15.3 mmol) was then added portionwise. After 2 hours stirring at room temperature, reaction mixture was treated successively with 2N NaOH (18 ml) and H$_2$O (50 ml). The aqueous phase was extracted with ethyl acetate (3×80 ml). Combined organic phases were dried over Na$_2$SO$_4$ and concentrated. The residue was chromatographed over silica gel (hexane-ethyl acetate, 9:1) to provide 3.4 g of a yellow oil. Addition of n-pentane provided 4-chloro-2-m-tolyl-quinoline (1.58 g, 41%) as a white solid, m. p. 75–77° C., MS: m/e=253 (M$^+$).

The following 4-chloroquinolines, which are known in the literature, have been prepared according to the General method of example 120:

4-chloro-2-p-tolyl-quinoline; 4-chloro-2-(4-methoxy-phenyl)-quinoline;
4-chloro-2-(4-methoxy-phenyl)-7-methyl-quinoline;
4-chloro-7-methoxy-2-phenyl-quinoline;
4-chloro-2-(4-chloro-phenyl)-quinoline;
4-chloro-2-naphthalen-2-yl-quinoline;
4-chloro-7-methyl-2-phenyl-quinoline; and
4,7-dichloro-2-phenyl-quinoline.

The following compounds of example 121 to 137, which are not known in the literature, have been prepared according to the general method of example 120

EXAMPLE 121

4-Chloro-2-(4-methoxy-3-methyl-phenyl)-quinoline

The title compound, m. p. 90–92° C., MS: m/e=283 (M$^+$), was prepared from 4-chloro-quinoline and 4-bromo-1-methoxy-2-methyl-benzene.

4-Bromo-1-methoxy-2-methyl-benzene is a known compound and has been prepared as described in the following reference: M. J. S. Dewar; N. A. Puttnam, J. Chem. Soc. 1960, 959–963.

EXAMPLE 122

4-Chloro-7-methyl-2-p-tolyl-quinoline

The title compound, m. p. 110–111 ° C., MS: m/e=267 (M$^+$), was prepared from 4-chloro-7-methyl-quinoline and 4-bromotoluene.

4-Chloro-7-methyl-quinoline is a known compound and has been prepared as described in the following reference: Breslow; J. Am. Chem. Soc, 68, 1946, 1232–1236

EXAMPLE 123

4-Chloro-2-(3-chloro-4-methyl-phenyl)-quinoline

The title compound, m. p. 115–116° C., MS: m/e=288 ($M^+$), was prepared from 4-chloroquinoline and 2-chloro-4-iodo-toluene.

EXAMPLE 124

4-Chloro-7-methoxy-2-(4-methoxy-phenyl)-quinoline

The title compound, m. p. 99–101° C., MS: m/e=299 ($M^+$), was prepared from 4-chloro-7-methoxy-quinoline and 4-bromoanisole.

4-Chloro-7-methoxy-quinoline is a known compound and has been prepared as described in the following reference: Lauer; J. Am. Chem. Soc, 68, 1946, 1268

EXAMPLE 125

4-Chloro-7-methoxy-2-p-tolyl-quinoline

The title compound, m. p. 129–131° C., MS: m/e=283 ($M^+$), was prepared from 4-chloro-7-methoxy-quinoline and 4-bromotoluene.

EXAMPLE 126

4-Chloro-2-(4-chloro-phenyl)-7-methoxy-quinoline

The title compound, m. p. 153–155° C., MS: m/e=305 ($M+H^+$), was prepared from 4-chloro-7-methoxy-quinoline and 1-bromo-4-chlorobenzene.

EXAMPLE 127

4-Chloro-2-(3-chloro-4-methoxy-phenyl)-quinoline

The title compound, m. p. 113–116 ° C., MS: m/e=304 ($M^+$), was prepared from 4-(chloro-quinoline and 4-bromo-2-chloro-1-methoxy-benzene.

4-Bromo-2-chloro-1-methoxy-benzene is a known compound and has been prepared as described in the following reference: E. A. Nodiff; J. Het. Chem.; 5, 1968, 165–167.

EXAMPLE 128

4-Chloro-2-(3,4-dimethyl-phenyl)-quinoline

The title compound, MS: m/e=267 ($M^+$), was prepared from 4-chloro-quinoline and 4-bromo-o-xylene.

EXAMPLE 129

4-Chloro-2-(2,3-dihydro-benzofuran-5-yl)-quinoline

The title compound, m. p. 130–132° C., MS: m/e=281 ($M^+$), was prepared from 4-chloro-quinoline and 5-iodo-2,3-dihydrobenzofuran.

5-Iodo-2,3-dihydrobenzofuran is a known compound and has been prepared as described in the following reference: A. Walser, T. Flynn, C. Mason, H. Crowley, C. Maresca, M. O'Donnell, J. Med. Chem., 34, 4, 1991, 1440–1446

EXAMPLE 130

4-Chloro-2-(3,4-dichloro-phenyl)-quinoline

The title compound, m. p. 138–140° C., MS: m/e=308 ($M^+$), was prepared from 4-chloro-quinoline and 3,4-dichloroiodobenzene.

EXAMPLE 131

4-Chloro-2-(3,4-dichloro-phenyl)-7-methoxy-quinoline

The title compound, m. p. 122–131° C., MS: m/e=338 ($M^+$), was prepared from 4-chloro-7-methoxyquinoline and 3,4-dichloroiodobenzene.

EXAMPLE 132

4-Chloro-2-chroman-6-yl-quinoline

The title compound, MS: m/e=295 ($M^+$), was prepared from 4-chloro-quinoline and 6-bromo-chroman.

6-Bromo-chroman is a known compound and has been prepared as described in the following reference: Maitte, Ann. Chim. (Paris), 9, 1954, 431, 446, 450

EXAMPLE 133

4-Chloro-2-(4-trifluoromethyl-phenyl)-quinoline

The title compound, m. p. 53–55° C., MS: m/e=307 ($M^+$), was prepared from 4-chloro-quinoline and 4-bromo-benzotrifluoride.

EXAMPLE 134

2-Benzofuran-2-yl-4-chloro-quinoline

The title compound, m. p. 148–149° C., MS: m/e=279 ($M^+$), was prepared from 4-chloro-quinoline and benzofuran.

EXAMPLE 135

[4-(4-Chloro-quinolin-2-yl)-phenyl]-dimethyl-amine

The title compound, MS: m/e=282 ($M^+$), was prepared from 4-chloro-quinoline and 4-bromo-N,N-dimethylaniline.

EXAMPLE 136

2-Benzo[b]thiophen-2-yl-4-chloro-quinoline

The title compound, m. p. 142–145° C., MS: m/e=295 ($M^+$), was prepared from 4-chloro-quinoline and 1-benzothiophene.

EXAMPLE 137

4-Chloro-2-thiophen-3-yl-quinoline

The title compound, MS: m/e=245 ($M^+$), was prepared from 4-chloro-quinoline and 3-bromothiophene.

By Reaction of a quinolin-4-one with phophorus oxychloride

EXAMPLE 138

2-lndan-5-yl-1H-quinolin-4-one

A mixture of 2-indan-5-yl-1H-quinolin-4-one (4.2 g, 16.1 mmol) and $POCl_3$ (6.3 ml, 67.5 mmol) was refluxed during 30 min. The reaction mixture was cooled to room temperature and added slowly to 2N NaOH (210 ml). After 2 hours of stirring, ethyl acetate was added. Aqueous phase was extracted with ethyl acetate (3×100 ml). Combined organic phases were dried over $Na_2SO_4$ and concentrated. The solid residue was stirred at 0° C. in the presence of $Et_2O$ (10 ml)

and then filtered to provide (2.0 g,45%) as a light green solid, m. p. 92–93° C., MS: m/e=279 (M⁺).

The following 4-chloro-quinolines, which are known in the literature, have been prepared according to the general method of example 138:

4-Chloro-8-methoxy-2-phenyl-quinoline: D. Bangdiwala; J. Indian Chem. Soc.; 31; 1954; 43–46;
4-Chloro-6-methoxy-2-phenyl-quinoline: Staskun; J. S. Afr. Chem. Inst.; 9; 1956; 89;
4-Chloro-6-methoxy-quinoline: Riegel; J. Am. Chem. Soc.; 68; 1946; 2685);
4-Chloro-7-methoxyquinoline and 4-Chloro-8-methoxy-quinoline: Lauer; J. Am. Chem. Soc.; 68; 1946; 1268);
4-Chloro-7-methyl-quinoline: Breslow; J. Am. Chem. Soc.; 68; 1946; 1232–1236);
4-Chloro-6-fluoroquinoline: Snyder; J. Am. Chem. Soc.; 69; 1947; 371–373);
4-Chloro-8-fluoroquinoline: Renault; Eur. J. Med. Chem. Chim. Ther.; 11; 1976; 555–559
4-Chloro-6-nitro-2-phenyl-quinoline: J. Stasku; J. Org. Chem.; 26; 1961; 3191

The following compounds of example 139 to 140, which are not known in the literature, have been prepared according to the general method of example 138.

EXAMPLE 139

4-Chloro-2-(5,6,7,8-tetrahydro-naphthalen-2-yl)-quinoline

The title compound, MS: m/e=293 (M⁺), was prepared from 2-(5,6,7,8-tetrahydro-naphthalen-2-yl)-1H-quinolin-4-one.

EXAMPLE 140

(RS)-4-Chloro-2-(1,2,3,4-tetrahydro-naphthalen-2-yl)-quinoline

The title compound, MS: m/e=293 (M⁺), was prepared from (RS)-2-(1,2,3,4-tetrahydro-naphthalen-2-yl)-1H-quinolin-4-one.

Preparation of the quinolin-4-ones

By Condensation of Derivatives of Anthranilic Acid and Acetophenone

EXAMPLE 141

2-Indan-5-yl-1H-quinolin-4-one

To a mixture of 5-acetylindane (3.0 g, 18.7 mmol) and anthranilic acid ethyl ester (2.8 ml, 18.7 mmol) in diphenylether (47 g) was added portionwise AlCl₃ (3.5 g, 26.2 mmol). The reaction mixture was stirred at 200° C. for 2.5 hours and cooled to room temperature. Hexane (100 ml) and MeOH (3 ml) were then added. The so obtained solid was filtered, washed with hexane and stirred in the presence of 5N HCl (85 ml) and acetone (10 ml). After filtration, the solid was again washed with H₂O, and stirred with MeOH (15 ml) for 30 min. Filtration provided 2-indan-5-yl-1 H-quinolin-4-one (4.35 g, 89%) as a light yellow solid, MS: m/e=261 (M⁺).

The following quinolin-4-ones, which are known in the literature, have been prepared according to the general method of example 141:

2-p-Tolyl-1H-quinolin-4-one;
2-(4-methoxy-phenyl)-1H-quinolin-4-one;

The compound of example 142 has been prepared according to the general method of example 141.

EXAMPLE 142

2-(5,6,7,8-Tetrahydro-naphthalen-2-yl)-1H-quinolin-4-one

The title compound, m. p. 241–250° C., MS: m/e=276.3 (M+H⁺), was prepared from 6-acetyltetraline.

By Condensation of an Aniline with a β-ketoester

EXAMPLE 143

(RS)-2-(1,2,3,4-Tetrahydro-naphthalen-2-yl)-1H-quinolin-4-one

A mixture containing aniline (0.7 ml, 7.7 mmol), p-toluene sulfonic acid (0.037 g,0.19 mmol) and (RS)-3-oxo-3-(1,2,3,4-tetrahydro-naphthalen-2-yl)-propionic acid ethyl ester (1.9 g, 7.7 mmol) in toluene (10 ml) was refluxed for 2.5 hours, and water was removed azeotropically. Reaction mixture was concentrated, diluted with diphenylether (8 ml), refluxed for 45 min., cooled to room temperature and diluted with Et₂O (150 ml). The resulting solid was filtered, washed with Et₂O and CH₂Cl₂ to provide (RS)-2-(1,2,3,4-Tetrahydro-naphthalen-2-yl)-1H-quinolin-4-one (0.67 g, 32%) as a light yellow solid, mp.>300° C., MS: m/e=275 (M⁺).

The following quinolin-4-ones, which are known in the literature, have been prepared according to the general method of example 143:

7-Methoxy-2-phenyl-1H -quinolin -4-one;
8-methoxy-2-phenyl-1H-quinolin-4-one;
2-phenyl-1H-quinolin-4-one;
6-fluoro-2-phenyl-1H-quinolin-4-one; and
6-methoxy-2-phenyl-1H-quinolin-4-one.

Preparation of Other Intermediates

EXAMPLE 144

(2RS,5RS) and (2RS,5SR) (3-Methyl-2-phenyl-oxazolidin-5-yl)-methanol

A mixture containing benzaldehyde (21.2 g, 0.2 mol) and (RS)-3-methylamino-1,2-propandiol (17.6 g, 0.167 mol) in toluene (110 ml) was refluxed for 3.5 hours. Mixture was then cooled to room temperature, concentrated and residue was distilled at 135° C. under 0.7 mbar pressure to provide a mixture of (2RS,5RS) and (2RS,5SR) (3-methyl-2-phenyl-oxazolidin-5-yl)-methanol (28.7 g 89%) as a colorless oil, MS: m/e=193 (M⁺).

EXAMPLE 145

(RS)-3-Oxo-3-(1,2,3,4-tetrahydro-naphthalen-2-yl)-propionic acid ethyl ester

A solution of malonic acid monoethyl ester (3.8 g, 29 mmol) in THF (80 ml) was cooled to −78° C. n-BuLi (36 ml, 58 mmol, 1.6 M in hexane) was added dropwise so that the temperature of the reaction mixture at the end the addition was −5° C. After 5 min. stirring at −5° C., reaction mixture was cooled to −65° C. and treated with a solution of (RS)-1,2,3,4-tetrahydro-naphthalene-2-carbonyl chloride (3.2 g, 16.5 mmol) in THF. Mixture was stirred for 10 min. at −65° C. and then added to a stirring mixture containing Et$_2$O (200 ml) and 1N HCl (100 ml). Aqueous phase was extracted with Et$_2$O (2×150 ml). Combined organic phases were washed successively with a saturated solution of NaHCO$_3$ (100 ml) and NaCl (100 ml), dried over Na$_2$SO$_4$ and concentrated to provide (RS)-3-oxo-3-(1,2,3,4-tetrahydro-naphthalen-2-yl)-propionic acid ethyl ester (3.8 g, 93%) as a light brown oil, MS: m/e=246 (M$^+$).

(RS)-1,2,3,4-Tetrahydro-naphthalene-2-carbonyl chloride is a known compound and has been prepared as described in the following reference: J. C. Morris; L. N. Mander; D. C. R. Hockless; Synthesis; 1998; 455–467

The structural formula set forth in Table 1, correspond to the compounds described in Examples 1 through 103 above.

| R$^1$ | R$^2$ | R$^3$ | R$^4$ | R$^5$ | X | X and R$^5$ are together | X and R$^3$ are together | Example Number |
|---|---|---|---|---|---|---|---|---|
| H | N-methyl-tetrahydroisoquinolin-yl | H | H | H | NH | — | — | 1 |
| 7-CH$_3$ | 4-CH$_3$-phenyl | H | H | —CH$_2$NH$_2$ | NH | — | — | 2 |
| H | 4-OCH$_3$-phenyl | H | H | —CH$_2$NH$_2$ | NH | — | — | 3 |
| H | 4-OCH$_3$-phenyl | H | H | —CH$_3$ | NH | — | — | 4 |
| 7-CH$_3$ | 4-OCH$_3$-phenyl | H | H | H | NH | — | — | 5 |
| H | 3-CH$_3$-4-OCH$_3$-phenyl | H | H | —CH$_3$ | NH | — | — | 6 |
| 7-CH$_3$ | 4-CH$_3$-phenyl | H | H | H | NH | — | — | 7 |
| H | 3-Cl-4-CH$_3$-phenyl | H | H | —CH$_3$ | NH | — | — | 8 |

-continued

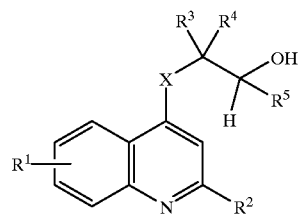

| R¹ | R² | R³ | R⁴ | R⁵ | X | X and R⁵ are together | X and R³ are together | Example Number |
|---|---|---|---|---|---|---|---|---|
| H | N-methyl-tetrahydroisoquinolinyl | H | H | —CH₂OH | NH | — | — | 9 |
| H | N-methyl-tetrahydroisoquinolinyl | H | H | —CH₂NH₂ | NH | — | — | 10 |
| 7-OCH₃ | 4-methoxyphenyl | H | H | H | NH | — | — | 11 |
| 7-OCH₃ | 4-methoxyphenyl | H | H | —CH₂NH₂ | NH | — | — | 12 |
| 7-OCH₃ | 4-methylphenyl | H | H | —CH₂NH₂ | NH | — | — | 13 |
| 7-CH₃ | 4-methoxyphenyl | H | H | —CH₃ | NH | — | — | 14 |
| H | styryl | H | H | —CH₂OH | NH | — | — | 15 |
| 7-OCH₃ | phenyl | H | H | H | NH | — | — | 16 |
| H | 4-methoxyphenyl | H | H | H | NH | — | — | 17 |
| H | tetrahydronaphthyl | H | H | H | NH | — | — | 18 |

-continued
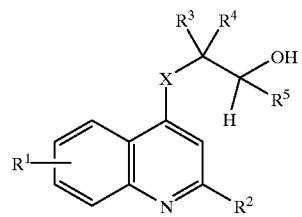
| R¹ | R² | R³ | R⁴ | R⁵ | X | X and R⁵ are together | X and R³ are together | Example Number |
|---|---|---|---|---|---|---|---|---|
| 7-CH₃ | 4-CH₃-C₆H₄ | H | H | —CH₃ | NH | — | — | 19 |
| H | 3-Cl-4-CH₃-C₆H₃ | H | H | —CH₂OH | NH | — | — | 20 |
| H | 4-CH₃-C₆H₄ | H | H | —CH₃ | NH | — | — | 21 |
| H | 4-OCH₃-C₆H₄ | H | H | —CH₂OH | NH | — | — | 22 |
| 7-OCH₃ | 4-Cl-C₆H₄ | H | H | —CH₂NH₂ | NH | — | — | 23 |
| 7-OCH₃ | 4-CH₃-C₆H₄ | H | H | H | NH | — | — | 24 |
| H | 3-Cl-4-CH₃-C₆H₃ | H | H | —CH₃ | NH | — | — | 25 |
| H | 4-CH₃-C₆H₄ | H | H | H | NH | — | — | 26 |
| H | 3,4-(CH₃)₂-C₆H₃ | H | H | —CH₂OH | NH | — | — | 27 |
| H | 4-CH₃-C₆H₄ | H | H | —CH₂OH | NH | — | — | 28 |

-continued

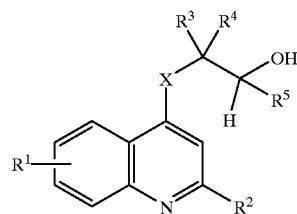

| R¹ | R² | R³ | R⁴ | R⁵ | X | X and R⁵ are together | X and R³ are together | Example Number |
|---|---|---|---|---|---|---|---|---|
| 7-OCH₃ | phenyl | H | H | —CH₂NH₂ | NH | — | — | 29 |
| H | 5,6,7,8-tetrahydronaphthalen-2-yl | H | H | —CH₂OH | NH | — | — | 30 |
| H | 3,4-dimethylphenyl | H | H | —CH₃ | NH | — | — | 31 |
| H | 3,4-dimethylphenyl | H | H | —CH₂OH | NH | — | — | 32 |
| 7-OCH₃ | phenyl | H | H | —CH₃ | NH | — | — | 33 |
| H | 3-methyl-4-methoxyphenyl | H | H | —CH₂OH | NH | — | — | 34 |
| 7-OCH₃ | phenyl | H | H | —CH₂OH | NH | — | — | 35 |
| H | 3,4-dichlorophenyl | H | H | —CH₂OH | NH | — | — | 36 |
| 7-OCH₃ | 4-chlorophenyl | H | H | H | NH | — | — | 37 |
| H | 3-chloro-4-methylphenyl | H | H | —CH₂OH | NH | — | — | 38 |

-continued
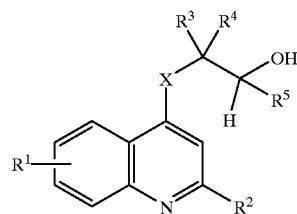
| R¹ | R² | R³ | R⁴ | R⁵ | X | X and R⁵ are together | X and R³ are together | Example Number |
|---|---|---|---|---|---|---|---|---|
| H | 4-Cl-C₆H₄ | H | H | H | NH | — | — | 39 |
| H | 3,4-di-Cl-C₆H₃ | H | H | —CH₂NH₂ | NH | — | — | 40 |
| 7-OCH₃ | 3,4-di-Cl-C₆H₃ | H | H | H | NH | — | — | 41 |
| 7-OCH₃ | 3,4-di-Cl-C₆H₃ | H | H | —CH₂NH₂ | NH | — | — | 42 |
| H | 4-OCH₃-C₆H₄ | H | H | — | — | —N(CH₃)(CH₂)₂— | — | 43 |
| H | 4-Cl-C₆H₄ | H | H | —CH₂NH₂ | NH | — | — | 44 |
| H | 6-chromanyl | H | H | —CH₂OH | NH | — | — | 45 |
| H | 4-OCH₃-C₆H₄ | H | H | H | NCH₃ | — | — | 46 |
| H | 2-naphthyl | H | H | —CH₂NH₂ | NH | — | — | 47 |
| H | 5-indanyl | H | H | —CH₂OH | NH | — | — | 48 |

-continued
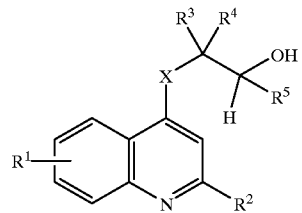
| R¹ | R² | R³ | R⁴ | R⁵ | X | X and R⁵ are together | X and R³ are together | Example Number |
|---|---|---|---|---|---|---|---|---|
| 7-CH₃ | phenyl | H | H | H | NH | — | — | 49 |
| H | 4-methoxyphenyl | — | H | H | — | — | —N(CH₃)(CH₂)₂— | 50 |
| 8-OCH₃ | phenyl | H | H | H | NH | — | — | 51 |
| H | 3,4-dichlorophenyl | H | H | H | NH | — | — | 52 |
| H | 4-methoxyphenyl | H | H | —CH₂N(CH₃)₂ | NH | — | — | 53 |
| H | N-methylisoindolinyl | H | H | —CH₂OH | NH | — | — | 54 |
| H | phenyl | H | H | —CH₂NH₂ | NH | — | — | 55 |
| H | 4-(trifluoromethyl)phenyl | H | H | —CH₂OH | NH | — | — | 56 |
| H | phenyl | H | H | —CH₃ | NH | — | — | 57 |
| H | 1,2,3,4-tetrahydronaphthalen-2-yl | H | H | —CH₂OH | NH | — | — | 58 |

-continued
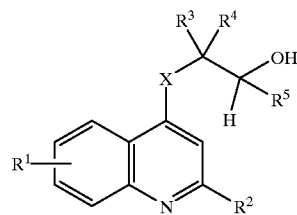
| R¹ | R² | R³ | R⁴ | R⁵ | X | X and R⁵ are together | X and R³ are together | Example Number |
|---|---|---|---|---|---|---|---|---|
| H | 4-Cl-C₆H₄ | H | H | —CH₂OH | NH | — | — | 59 |
| H | C₆H₅ | H | H | H | NH | — | — | 60 |
| 8-OCH₃ | C₆H₅ | H | H | —CH₂OH | NH | — | — | 61 |
| 7-OH | C₆H₅ | H | H | —CH₂OH | NH | — | — | 62 |
| H | 2-benzofuranyl | H | H | —CH₂OH | NH | — | — | 63 |
| H | 3-CH₃-C₆H₄ | H | H | —CH₂OH | NH | — | — | 64 |
| H | 4-Cl-C₆H₄ | H | H | —CH₂NH₂ | NH | — | — | 65 |
| H | 4-OCH₃-C₆H₄ | H | H | — | — | —N(CH₂)₂— | — | 66 |
| H | 4-N(CH₃)₂-C₆H₄ | H | H | —CH₂OH | NH | — | — | 67 |
| 6-OH | C₆H₅ | H | H | —CH₂OH | NH | — | — | 68 |

-continued
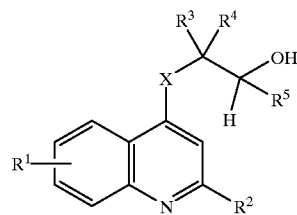
| R¹ | R² | R³ | R⁴ | R⁵ | X | X and R⁵ are together | X and R³ are together | Example Number |
|---|---|---|---|---|---|---|---|---|
| H | phenyl | H | H | —CH₂OH | NH | — | — | 69 |
| H | phenyl | H | H | —CH₃ | NH | — | — | 70 |
| H | phenyl | H | H | — | — | —N(CH₃)(CH₂)₂— | — | 71 |
| H | 2,3-dihydrobenzothiophen-2-yl | H | H | —CH₂OH | NH | — | — | 72 |
| 7-Cl | phenyl | H | H | —CH₂OH | NH | — | — | 73 |
| H | 4-methoxyphenyl | H | H | —CH₂-piperidinyl | NH | — | — | 74 |
| H | 2-phenylethyl | H | H | —CH₂OH | NH | — | — | 75 |
| 6-NH₂ | phenyl | H | H | —CH₂OH | NH | — | — | 76 |
| H | 4-methoxyphenyl | H | H | —CH₂NHCH₃ | NH | — | — | 77 |
| 7-OCH₃ | 4-methylphenyl | H | H | —CH₂NHCH₃ | NH | — | — | 78 |

-continued
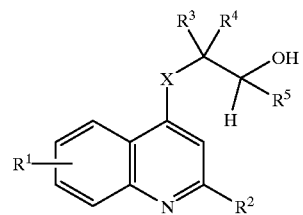
| R¹ | R² | R³ | R⁴ | R⁵ | X | X and R⁵ are together | X and R³ are together | Example Number |
|---|---|---|---|---|---|---|---|---|
| 7-OCH₃ | 4-Cl-C₆H₄ | H | H | —CH₂NHCH₃ | NH | — | — | 79 |
| H | C₆H₅ | H | H | —CH₂NHCH₃ | NH | — | — | 80 |
| H | C₆H₅ | H | H | —CH₂NH(CH₂)₂—C₆H₅ | NH | — | — | 81 |
| H | C₆H₅ | H | H | CH₂NH(CH₂)₂—C₆H₅ | NH | — | — | 82 |
| 7-OCH₃ | C₆H₅ | H | H | —CH₂NHCH₃ | O | — | — | 83 |
| H | C₆H₅ | H | H | —CH₂NH₂ | O | — | — | 84 |
| H | C₆H₅ | H | H | —CH₂NHCH—(CH₃)₂ | O | — | — | 85 |
| H | C₆H₅ | H | H | —CH₂NH-cyclopentyl | O | — | — | 86 |
| 7-OCH₃ | C₆H₅ | H | H | —CH₂NHCH—(CH₃)₂ | O | — | — | 87 |
| H | 4-CH₃-C₆H₄ | H | H | —CH₂NHCH₃ | O | — | — | 88 |

-continued

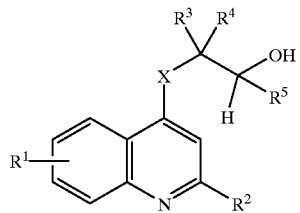

| R¹ | R² | R³ | R⁴ | R⁵ | X | X and R⁵ are together | X and R³ are together | Example Number |
|---|---|---|---|---|---|---|---|---|
| H | phenyl | H | H | —CH₂NH-cyclobutyl | O | — | — | 89 |
| H | 4-methoxyphenyl | H | H | —CH₂NHCH₃ | O | — | — | 90 |
| 6-F | phenyl | H | H | —CH₂NHCH₃ | O | — | — | 91 |
| H | phenyl | H | H | (CH₂)₃NCH₂— (morpholino) | O | — | — | 92 |
| H | phenyl | H | H | —CH₂NHCH₂—CH₃ | O | — | — | 93 |
| H | phenyl | H | H | —CH₂NH-cyclopropyl | O | — | — | 94 |
| H | phenyl | H | H | CH₂NH(CH₂)₃—CH₃ | O | — | — | 95 |
| 7-CH₃ | phenyl | H | H | —CH₂NHCH₃ | O | — | — | 96 |
| 7-OCH₃ | 4-methylphenyl | H | H | —CH₂NHCH₃ | O | — | — | 97 |
| 7-OCH₃ | 4-methoxyphenyl | H | H | —CH₂NHCH₃ | O | — | — | 98 |

-continued

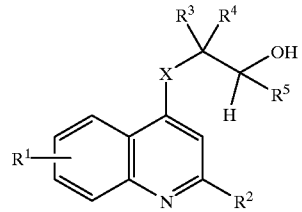

| R¹ | R² | R³ | R⁴ | R⁵ | X | X and R⁵ are together | X and R³ are together | Example Number |
|---|---|---|---|---|---|---|---|---|
| 7-CH₃ | 4-methoxyphenyl | H | H | —CH₂NHCH₃ | O | — | — | 99 |
| 7-CH₃ | 4-methylphenyl | H | H | —CH₂NHCH₃ | O | — | — | 100 |
| H | N-methyl-tetrahydroisoquinolinyl | H | H | —CH₂NHCH₃ | O | — | — | 101 |
| 7-Cl | phenyl | H | H | —CH₂NHCH₃ | O | — | — | 102 |
| H | phenyl | H | H | —CH₂NHCH₃ | O | — | — | 103 |

Example A

Tablet Formulation (Wet Granulation)

|  |  | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure

1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

Example B

Capsule Formulation

|  |  | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure

1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:

1. A compound of formula I:

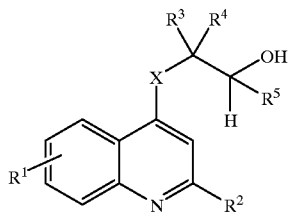

wherein
is hydrogen, lower alkyl, lower alkoxy, hydroxy, amino, nitro, cyano, lower alkyl-amino, di-lower alkyl-amino or halogen;

$R^2$ is 2,3-dihydro-benzofuran-5-yl, chroman-6-yl, naphthalen-2-yl, indan-5-yl, lower alkenyl-phenyl, 5,6,7,8-tetrahydro-naphthalenyl, 2,3-dihydro-isoindol-2-yl, 1,2,3,4-tetrahydro-naphthalenyl, benzofuran-2-yl, benzo[b]thiophen-2-yl, lower alkyl-phenyl, 3,4-dihydro-1H-isoquinolin-2-yl or thiophen-3-yl, or is unsubstituted phenyl, or phenyl substituted by lower alkyl, lower alkoxy, halogen, trifluoromethyl, amino, lower alkyl-amino or di-lower alkyl-amino;

$R^3$ and $R^4$ are independently from each other hydrogen or lower alkyl;

$R^5$ is hydrogen, lower alkyl, —$CH_2OH$ or —$CH_2NR^6R^7$;

$R^6$ and $R^7$ are independently from each other hydrogen, lower alkyl, —$(CH_2)_n$-phenyl, cycloalkyl, —$(CH_2)_m$-morpholinyl or form together with the N-atom a saturated ring with 4–6 C-atoms;

n is 0–3;

m is 2 or 3;

X is —$NR^8$— or —O—; or

X and $R^5$ are together >$N(CH_2)_2$—; or

X and $R^3$ are together >$N(CH_2)_3$—; and $R^8$ is hydrogen or lower alkyl;

or a pharmaceutically acceptable acid addition salt thereof, with the exception of the following compounds (6-chloro-2-phenyl-4-quinolinyl)-(+)-2-aminobutanol,
(6-methyl-2-phenyl-4-quinolinyl)-(+)-2-aminobutanol,
(6-methoxy-2-phenyl-4-quinolinyl)-(+)-2-aminobutanol and
(8-methoxy-2-phenyl-4-quinolinyl)-(+)-2-aminobutanol.

2. A compound according to claim 1, wherein X is —NH—.

3. A compound according to claim 2, 2-[2-(3,4-dihydro-1H-isoquinolin-2-yl)-quinolin-4-ylamino]-ethanol.

4. A compound according to claim 2, (RS)-1-amino-3-(2-p-tolyl-quinolin-4-ylamino)-propan-2-ol.

5. A compound according to claim 2, (RS)-1-amino-3-[2-(4-methoxy-phenyl)-quinolin-4-ylamino]-propan-2-ol.

6. A compound according to claim 2, S(+)-1-[2-(4-methoxy-phenyl)-quinolin-4-ylamino]-propan-2-ol.

7. A compound according to claim 2, 2-[2-(4-methoxy-phenyl)-7-methyl-quinolin-4-ylamino]-ethanol.

8. A compound according to claim 2, (S)-1-[2-(4-methoxy-3-methyl-phenyl)-quinolin-4-ylamino]-propan-2-ol.

9. A compound according to claim 2, 2-(7-methyl-2-p-tolyl-quinolin-4-ylamino)-ethanol.

10. A compound according to claim 2, (S)-1-[2-(3-chloro-4-methyl-phenyl)-quinolin-4-ylamino]-propan-2-ol.

11. A compound according to claim 2, (RS)-3-[2-(3,4-dihydro-1H-isoquinolin-2-yl)-quinolin-4-ylamino]-propane-2-diol.

12. A compound according to claim 2, (RS)-1-amino-3-[2-(3,4-dihydro-1H-isoquinolin-2-yl)-quinolin-4-ylamino]-propan-2-ol.

13. A compound according to claim 2, 2-[7-methoxy-2-(4-methoxy-phenyl)-quinolin-4-ylamino]-ethanol.

14. A compound according to claim 2, (RS)-1-amino-3-[7-methoxy-2-(4-methoxy-phenyl)-quinolin-4-ylamino]-propan-2-ol.

15. A compound according to claim 2, (RS)-1-amino-3-(7-methoxy-2-p-tolyl-quinolin-4-ylamino)-propan-2-ol.

16. A compound according to claim 1, wherein X is —O—.

17. A compound according to claim 16, (RS)-1-(7-methoxy-2-phenyl-quinolin-4-yloxy)-3-methylamino-propan-2-ol.

18. A compound according to claim 16, (RS)-1-Amino-3-(2-phenyl-quinolin-4-yloxy)-propan-2-ol.

19. A compound according to claim 16, (RS)-1-Isopropylamino-3-(2-phenyl-quinolin-4-yloxy)-propan-2-ol.

20. A compound according to claim 16, (RS)-1-Cyclopentylamino-3-(2-phenyl-quinolin-4-yloxy)-propan-2-ol.

21. A compound according to claim 16, (RS)-1-Isopropylamino-3-(7-methoxy-2-phenyl-quinolin-4-yloxy)-propan-2-ol.

22. A compound according to claim 16, (RS)-1-Methylamino-3-(2-p-tolyl-quinolin-4-yloxy)-propan-2-ol.

23. A compound according to claim 16, (RS)-1-Cyclobutylamino-3-(2-phenyl-quinolin-4-yloxy)-propan-2-ol.

24. A compound according to claim 16, (RS)-1-[2-(4-Methoxy-phenyl)-quinolin-4-yloxy]-3-methylamino-propan-2-ol.

25. A compound according to claim 16, (RS)-1-Methylamino-3-(7-methyl-2-phenyl-quinolin-4-yloxy)-propan-2-ol.

26. A compound according to claim 16, (RS)-1-(7-Methoxy-2-p-tolyl-quinolin-4-yloxy)-3-methylamino-propan-2-ol.

27. A compound according to claim 16, (RS)-1-[7-Methoxy-2-(4-methoxy-phenyl)-quinolin-4-yloxy]-3-methylamino-propan-2-ol.

28. A compound according to claim 16, (RS)-1-[2-(4-Methoxy-phenyl)-7-methyl-quinolin-4-yloxy]-3-methylamino-propan-2-ol.

29. A pharmaceutical composition comprising a therapeutically effective amount of a compound of formula I of claim 1 or a pharmaceutically acceptable salt of said compound and a pharmaceutically acceptable carrier.

30. A method of treating acute and chronic neurodegeneration in a mammal comprising administering to said mammal a compound of the formula I of claim 1 and a pharmaceutically acceptable carrier in an amount which is effective in treating the neurodegeneration.

31. A process for preparing a compound of formula I of claim 1, comprising reacting a compound of formula:

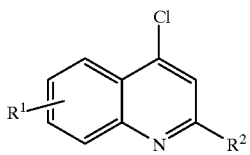

with an amine of formula:

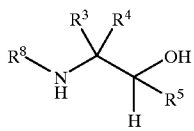

to form a compound of formula:

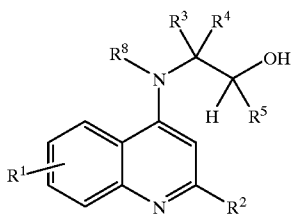

wherein

R¹ is hydrogen, lower alkyl, lower alkoxy, hydroxy, amino, nitro, cyano, lower alkyl-amino, di-lower alkyl-amino or halogen;

R² is 2,3-dihydro-benzofuran-5-yl, chroman-6-yl, naphthalen-2-yl, indan-5-yl, lower alkenyl-phenyl, 5,6,7,8-tetrahydro-naphthalenyl, 2,3-dihydro-isoindol-2-yl, 1,2,3,4-tetrahydro-naphthalenyl, benzofuran-2-yl, benzo[b]thiophen-2-yl, lower alkyl-phenyl, 3,4-dihydro-1H-isoquinolin-2-yl or thiophen-3-yl, or is unsubstituted phenyl, or phenyl substituted by lower alkyl, lower alkoxy, halogen, trifluoromethyl, amino, lower alkyl-amino or di-lower alkyl-amino;

R³ and R⁴ are independently from each other hydrogen or lower alkyl;

R⁵ is hydrogen, lower alkyl, —CH₂OH or —CH₂NR⁶R⁷; and

R⁸ is hydrogen or lower alkyl.

32. A process for preparing a compound of formula I of claim 1, comprising:

reducing a compound of formula:

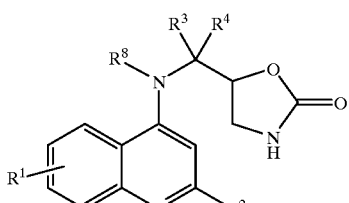

with a reducing agent to a compound of formula:

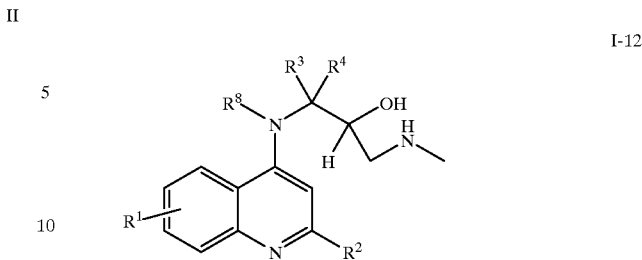

wherein

R¹ is hydrogen, lower alkyl, lower alkoxy, hydroxy, amino, nitro, cyano, lower alkyl-amino, di-lower alkyl-amino or halogen;

R² is 2,3-dihydro-benzofuran-5-yl, chroman-6-yl, naphthalen-2-yl, indan-5-yl, lower alkenyl-phenyl, 5,6,7,8-tetrahydro-naphthalenyl, 2,3-dihydro-isoindol-2-yl, 1,2,3,4-tetrahydro-naphthalenyl, benzofuran-2-yl, benzo[b]thiophen-2-yl, lower alkyl-phenyl, 3,4-dihydro-1H-isoquinolin-2-yl or thiophen-3-yl, or is unsubstituted phenyl, or phenyl substituted by lower alkyl, lower alkoxy, halogen, trifluoromethyl, amino, lower alkyl-amino or di-lower alkyl-amino;

R³ and R⁴ are independently from each other hydrogen or lower alkyl; and

R⁸ is hydrogen or lower alkyl.

33. A process for preparing a compound of formula I of claim 1, comprising: reducing a compound of formula:

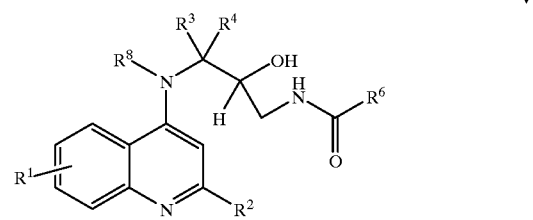

wherein R¹–R⁴ and R⁸ have the significances given in claim 32 and R⁶ is lower alkyl-phenyl, lower alkyl-morpholino or lower alkyl, to a compound of formula

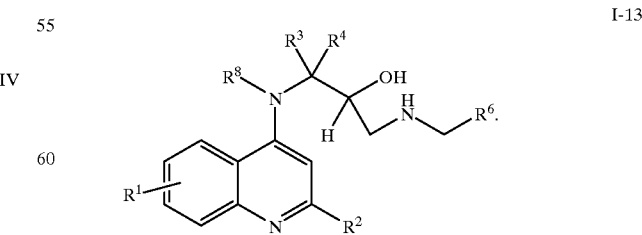

34. A process for preparing a compound of formula I of claim 1, comprising reacting a compound of formula:

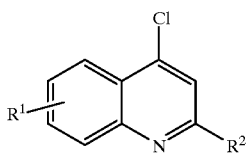
II
with a compound of formula:
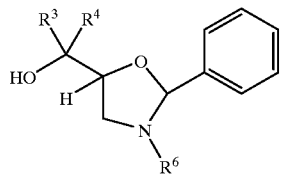
VI
to a compound of formula:
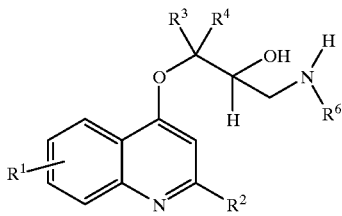
I-2
wherein $R^1$–$R^4$ and $R^6$ have the significances given in claim 32.
35. A process for preparing a compound of formula I of claim 1, comprising reacting a compound of formula:
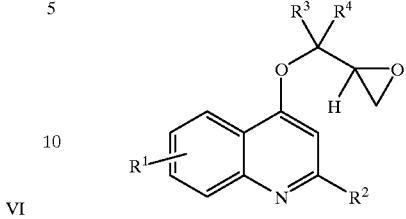
IX
with a compound of formula:
H—NR$^6$
to a compound of formula:
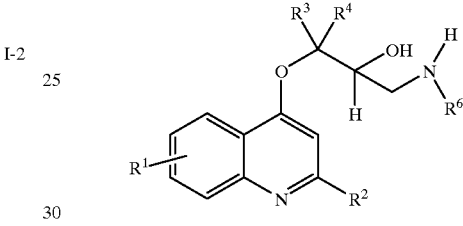
I-2
wherein $R^1$–$R^4$ and $R^6$ have the significances given in claim 32.
* * * * *